(12) United States Patent
Segawa et al.

(10) Patent No.: US 8,460,174 B2
(45) Date of Patent: Jun. 11, 2013

(54) CAPSULE MEDICAL APPARATUS WITH BOARD-SEPARATION KEEPING UNITS

(75) Inventors: Hidetake Segawa, Hachioji (JP); Kanako Kataoka, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 871 days.

(21) Appl. No.: 12/564,299

(22) Filed: Sep. 22, 2009

(65) Prior Publication Data

US 2010/0076258 A1   Mar. 25, 2010

(30) Foreign Application Priority Data

Sep. 22, 2008   (JP) ................... 2008-242435

(51) Int. Cl.
*A61B 1/00* (2006.01)
*A61B 1/04* (2006.01)
*H05K 7/00* (2006.01)
*H05K 5/00* (2006.01)

(52) U.S. Cl.
USPC .. 600/101; 600/130; 361/679.58; 361/679.43

(58) Field of Classification Search
USPC ............... 600/101, 109, 117, 118, 160, 179, 600/130, 129, 176; 174/525; 607/60; 348/340; 361/801, 737, 679.58, 679.43
See application file for complete search history.

(56) References Cited

U.S. PATENT DOCUMENTS

| | | | |
|---|---|---|---|
| 4,533,787 A * | 8/1985 | Anderegg et al. | 174/251 |
| 6,940,158 B2 * | 9/2005 | Haba et al. | 257/686 |
| 7,350,288 B2 * | 4/2008 | Sanders et al. | 29/739 |
| 2001/0006252 A1 * | 7/2001 | Kim et al. | 257/688 |
| 2001/0040793 A1 * | 11/2001 | Inaba | 361/749 |
| 2002/0096980 A1 * | 7/2002 | Montagna | 312/223.1 |
| 2004/0092025 A1 * | 5/2004 | Mordekhay | 436/55 |
| 2004/0104470 A1 * | 6/2004 | Bang et al. | 257/724 |
| 2005/0075684 A1 * | 4/2005 | Phillips et al. | 607/60 |
| 2005/0075685 A1 * | 4/2005 | Forsberg et al. | 607/60 |
| 2005/0075686 A1 * | 4/2005 | Phillips et al. | 607/60 |
| 2005/0075687 A1 * | 4/2005 | Phillips et al. | 607/60 |
| 2005/0075688 A1 * | 4/2005 | Toy et al. | 607/60 |
| 2005/0075689 A1 * | 4/2005 | Toy et al. | 607/60 |
| 2005/0075691 A1 * | 4/2005 | Phillips et al. | 607/60 |
| 2005/0075692 A1 * | 4/2005 | Schommer et al. | 607/60 |
| 2005/0224993 A1 * | 10/2005 | Manepalli et al. | 257/787 |
| 2006/0004276 A1 * | 1/2006 | Iddan et al. | 600/407 |

(Continued)

FOREIGN PATENT DOCUMENTS

| | | |
|---|---|---|
| JP | 2001-104287 | 4/2001 |
| JP | 2001-161627 A | 6/2001 |

(Continued)

OTHER PUBLICATIONS

Extended European Search Report dated Jan. 21, 2010.

(Continued)

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A capsule medical apparatus includes a plurality of rigid boards on which functional members are mounted; and a plurality of board-separation keeping units that sandwich the rigid boards to keep the rigid boards separated.

8 Claims, 24 Drawing Sheets

U.S. PATENT DOCUMENTS

| | | | |
|---|---|---|---|
| 2006/0008949 A1* | 1/2006 | Salta, III | 438/125 |
| 2006/0149132 A1* | 7/2006 | Iddan | 600/160 |
| 2006/0264703 A1* | 11/2006 | Fujimori | 600/101 |
| 2006/0264709 A1* | 11/2006 | Fujimori et al. | 600/130 |
| 2006/0276857 A1* | 12/2006 | Forsberg et al. | 607/60 |
| 2007/0032114 A1* | 2/2007 | Sanders et al. | 439/260 |
| 2007/0060955 A1* | 3/2007 | Strother et al. | 607/2 |
| 2007/0060967 A1* | 3/2007 | Strother et al. | 607/31 |
| 2007/0060968 A1* | 3/2007 | Strother et al. | 607/34 |
| 2007/0060979 A1* | 3/2007 | Strother et al. | 607/60 |
| 2007/0060980 A1* | 3/2007 | Strother et al. | 607/61 |
| 2007/0066995 A1* | 3/2007 | Strother et al. | 607/2 |
| 2007/0067000 A1* | 3/2007 | Strother et al. | 607/36 |
| 2007/0118012 A1* | 5/2007 | Gilad | 600/109 |
| 2007/0229656 A1 | 10/2007 | Khait et al. | |
| 2007/0230155 A1* | 10/2007 | Christol et al. | 361/816 |
| 2007/0259538 A1* | 11/2007 | Brodsky et al. | 439/66 |
| 2007/0288068 A1* | 12/2007 | Toy et al. | 607/60 |
| 2008/0074850 A1* | 3/2008 | Kuo | 361/740 |
| 2008/0102663 A1* | 5/2008 | Sakai | 439/108 |
| 2008/0234628 A1* | 9/2008 | Dent et al. | 604/20 |
| 2008/0312504 A1* | 12/2008 | Kimoto | 600/118 |
| 2009/0062605 A1* | 3/2009 | Orihara et al. | 600/109 |

FOREIGN PATENT DOCUMENTS

| | | |
|---|---|---|
| JP | 2001-332832 A | 11/2001 |
| JP | 2005-6769 A | 1/2005 |
| JP | 2005-204926 | 8/2005 |
| JP | 2005-287762 A | 10/2005 |
| JP | 2006-20852 A | 1/2006 |
| JP | 2006-130164 | 5/2006 |
| JP | 2006-141897 | 6/2006 |
| JP | 2007-123676 | 5/2007 |
| JP | 2007-143848 A | 6/2007 |
| JP | 2007-181516 A | 7/2007 |
| JP | 2007-185522 A | 7/2007 |
| JP | 2007-268293 A | 10/2007 |
| JP | 2007-274689 A | 10/2007 |
| JP | 2009-18077 A | 1/2009 |
| WO | WO 2006/070360 A1 | 7/2006 |

OTHER PUBLICATIONS

Notice of Rejection dated Jan. 22, 2013 from corresponding Japanese Patent Application No. 2008-242435 together with an English-language translation.

* cited by examiner

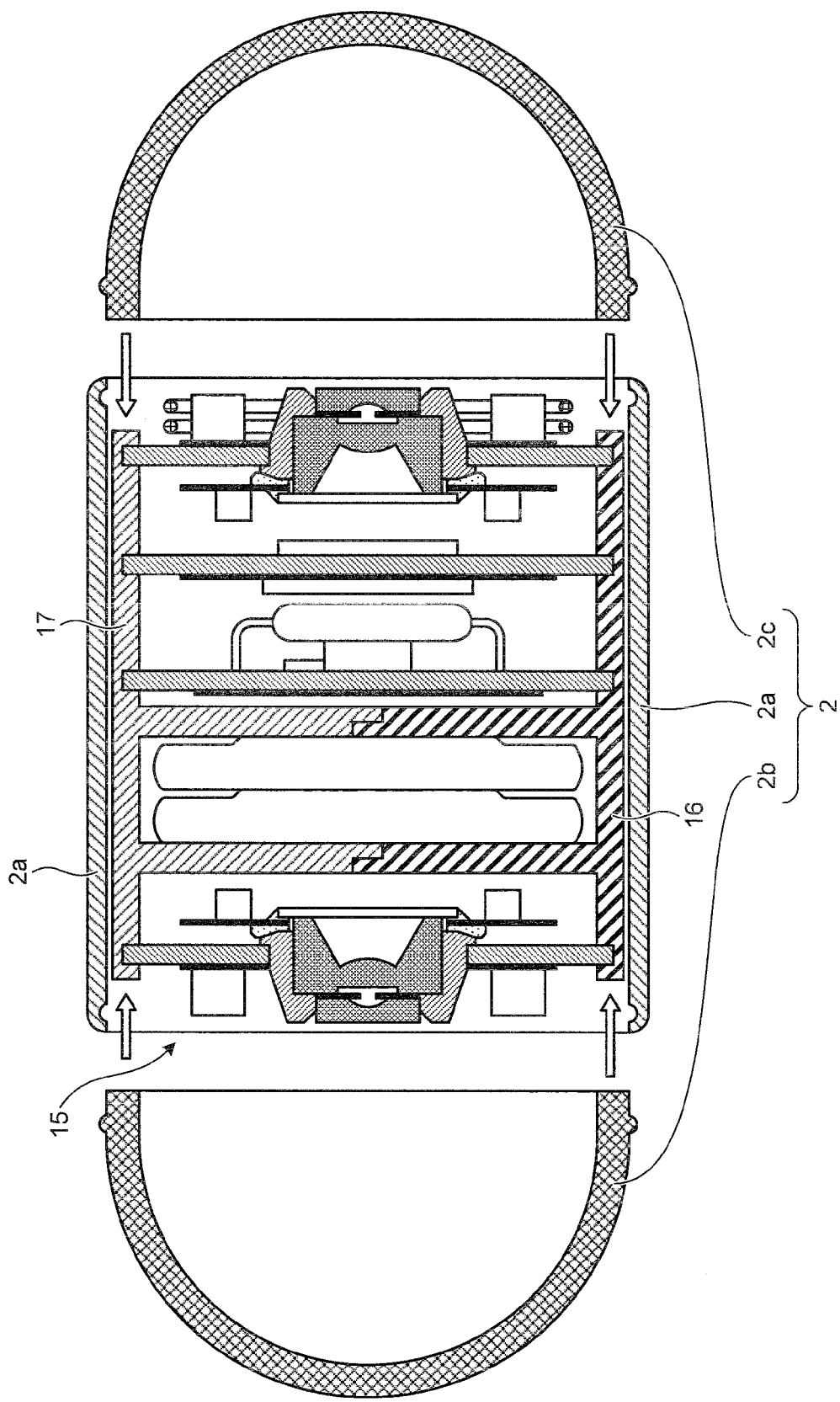

CAPSULE MEDICAL APPARATUS WITH BOARD-SEPARATION KEEPING UNITS

CROSS-REFERENCE TO RELATED APPLICATIONS

This application is based upon and claims the benefit of priority from Japanese Patent Application No. 2008-242435, filed Sep. 22, 2008, the entire contents of which are incorporated herein by reference.

BACKGROUND OF THE INVENTION

1. Field of the Invention

The present invention relates to a capsule medical apparatus that is introduced into the internal organs of a subject, such as a patient, and a method of manufacturing the capsule medical apparatus.

2. Description of the Related Art

Capsule medical apparatuses that have image-taking and wireless-communication functions are commonly used in the field of endoscopy. A capsule medical apparatus is introduced into a subject, such as a patient, from the mouth in order to observe the interior of the internal organs of the subject. The capsule medical apparatus in the subject sequentially takes in-vivo images of the internal organs (hereinafter, sometimes referred to as "in-vivo images") at predetermined intervals while moving through the internal organs by peristalsis. The capsule medical apparatus sequentially transmits the in-vivo images to the outside. The capsule medical apparatus repeatedly takes and wirelessly transmits in-vivo images over a period of time until it is excreted by the subject.

A group of in-vivo images that are taken by the capsule medical apparatus is received by a receiving apparatus outside the subject and stored in a portable recording medium in the receiving apparatus. The portable recording medium that stores therein the in-vivo images of the subject is detached from the receiving apparatus and then attached to an image display apparatus. The image display apparatus loads the group of in-vivo images from the portable recording medium and displays each of the loaded images on its display. Users, such as a doctor or a nurse, observe the interior of the internal organs of the subject by observing each in-vivo image that is displayed on the image display apparatus. On the basis of the observation result, the users can diagnose the subject.

Such capsule medical apparatuses include a capsule medical apparatus that has a structure that is sealed in a capsule-shaped outer casing and in which ring-shaped holders are alternately arranged between a plurality of rigid boards, such as an illumination board and an imaging board (see Japanese Patent Application Laid-open No. 2006-141897). In the process for assembling a capsule endoscope disclosed in Japanese Patent Application Laid-open No. 2006-141897, the rigid boards, which serve as function achieving units, are alternately superposed on the ring-shaped holders. The ring-shaped holders interposed between the rigid boards keep the rigid boards separated.

SUMMARY OF THE INVENTION

A capsule medical apparatus according to an aspect of the present invention includes a plurality of rigid boards on which functional parts are mounted; and a plurality of board-separation keeping units that sandwich the rigid boards to keep the rigid boards separated.

A method of manufacturing a capsule medical apparatus according to another aspect of the present invention includes assembling internal parts that include at least a plurality of rigid boards; keeping the rigid boards separated by sandwiching the internal parts between the rigid boards and sandwiching the rigid boards, using a plurality of board-separation keeping units; and sealing in a casing the internal parts that are sandwiched by the board-separation keeping units.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a schematic diagram representing that the internal parts that are sandwiched by the part holders in a pair are housed in a capsule-shaped casing;

DETAILED DESCRIPTION OF THE PREFERRED EMBODIMENTS

Exemplary embodiments of the present invention will be explained in detail with reference to the accompanying drawings. The embodiments are explained, taking as examples capsule medical apparatuses that are introduced into a subject and have an image-taking function of taking an in-vivo image, which is an example of in-vivo information about a subject, and a wireless-communication function of wirelessly transmitting the in-vivo image. However, the present invention is not limited to the embodiments.

First Embodiment

Figure 1:
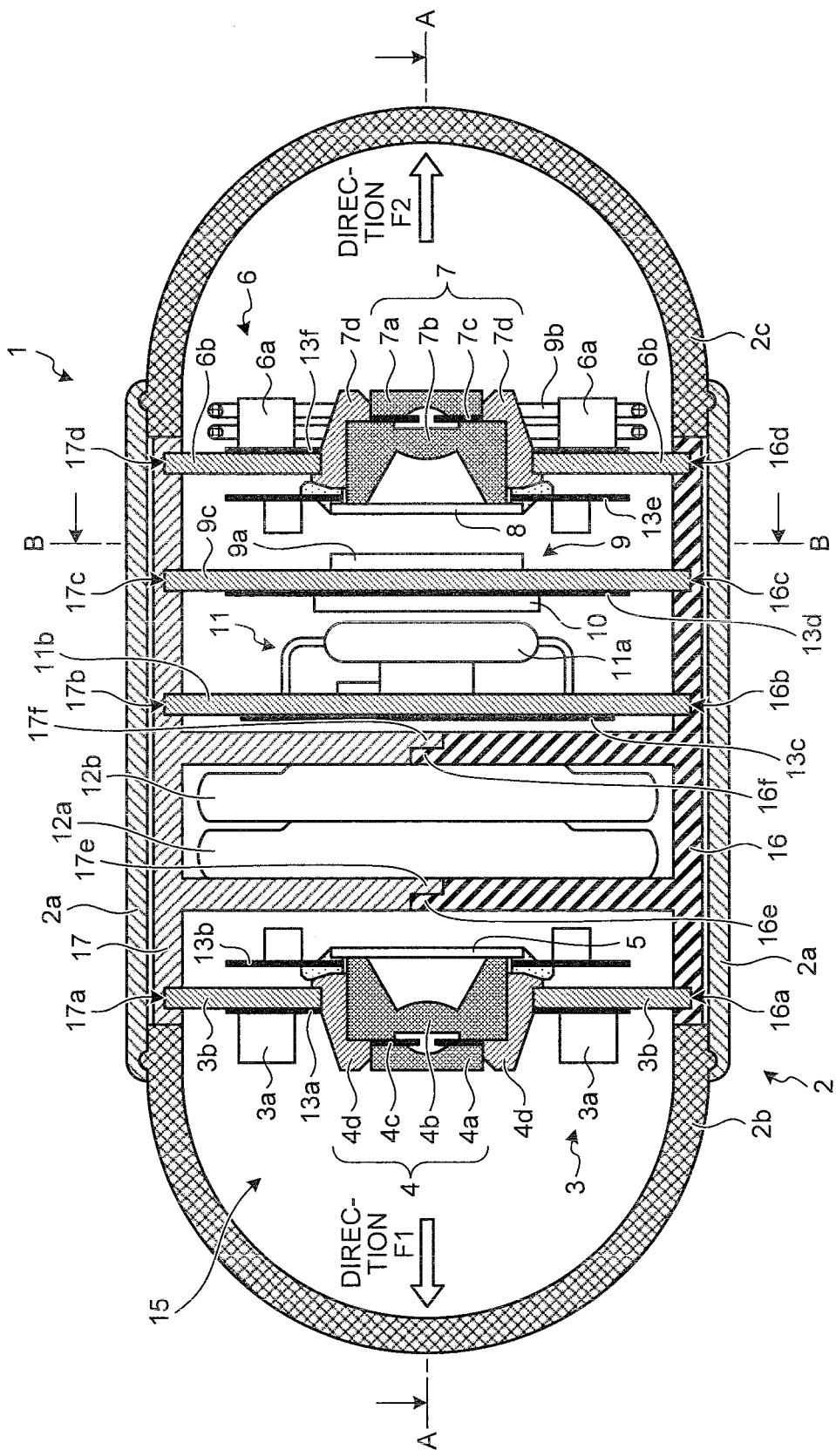
FIG. 1 is a schematic cross-sectional view that represents a configuration example of a capsule medical apparatus according to a first embodiment of the present invention.
Figure 2:
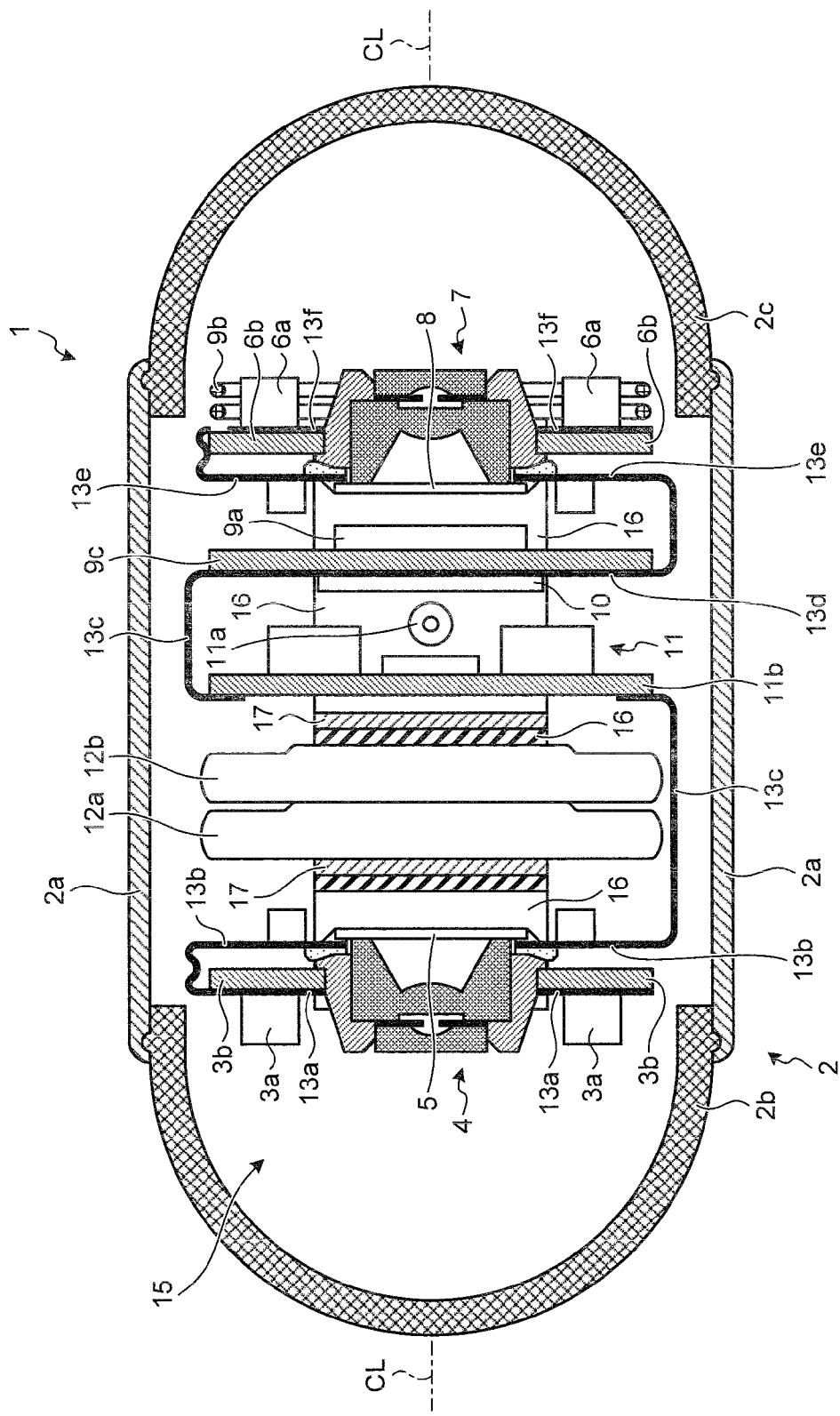
FIG. 2 is a schematic cross-sectional view, taken along A-A line, of the capsule medical apparatus illustrated in FIG. 1.
Figure 3:
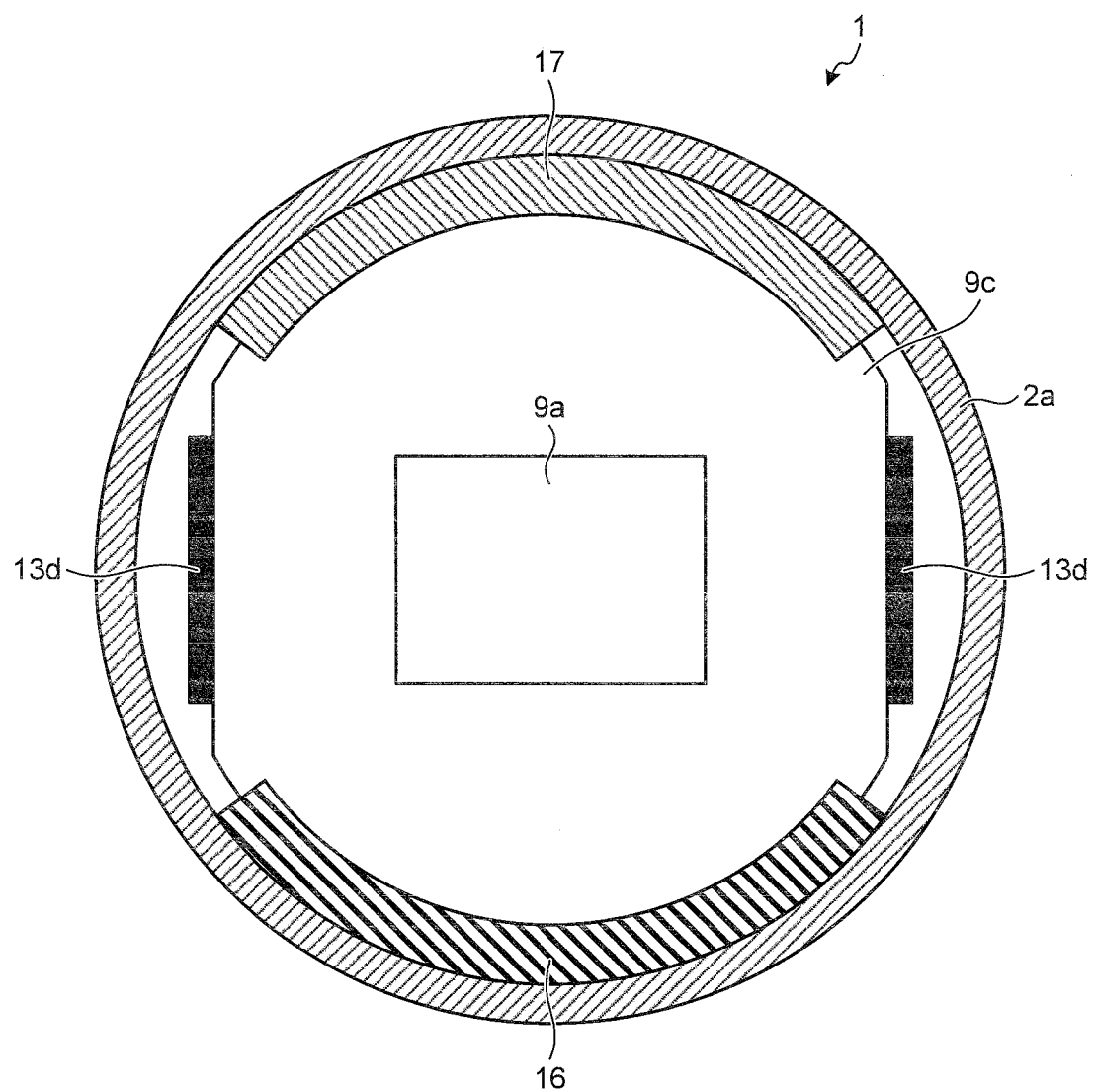
FIG. 3 is a schematic cross-sectional view, taken along B-B line, of the capsule medical apparatus illustrated in FIG. 1.

FIG. 1 is a schematic cross-sectional view that represents a configuration example of a capsule medical apparatus according to a first embodiment of the present invention. FIG. 2 is a schematic cross-sectional view, taken along A-A line, of the capsule medical apparatus illustrated in FIG. 1. FIG. 3 is a schematic cross-sectional view, taken along B-B line, of the capsule medical apparatus illustrated in FIG. 1.

As illustrated in FIGS. 1 to 3, a capsule medical apparatus 1 according to the first embodiment includes a capsule-shaped casing 2; an illuminating unit 3 that illuminates an object on the F1-direction side; an optical system 4 that forms an image of the object that is illuminated by the illuminating unit 3; and a solid-state imaging device 5 that takes an image of the subject that is formed by the optical system 4 (in-vivo image on the F1-direction side). The capsule medical apparatus 1 further includes an illuminating unit 6 that illuminates an object on the F2-direction side; an optical system 7 that forms an image of the object that is illuminated by the illuminating unit 6; and a solid-state imaging device 8 that takes an image of the object that is formed by the optical system 7 (in-vivo image on the F-2 direction side). The capsule medical apparatus 1 further includes a wireless communication unit 9 that wirelessly transmits each in-vivo image that is taken by the solid-state imaging device 5 or the solid-state imaging device 8 to the outside; a control unit 10 that controls the image-taking function and the wireless communication function; a power supply controller 11 that controls on/off of power supply; and batteries 12a and 12b that supply electric power to functional parts of the capsule medical apparatus 1. The capsule medical apparatus 1 further includes rigid boards 3b, 6b, 9c, and 11b and flexible boards 13a to 13f on which various functional parts are mounted; and a pair of part holders 16 and 17 that sandwich the rigid boards 3b, 6b, 9c, and 11b.

The capsule-shaped casing 2 is formed in a size such that it can be introduced to the internal organs of a subject, such as a patient. The edges of openings of a cylindrical casing 2a on both sides are closed with dome-shaped casings 2b and 2c, so that the capsule-shaped casing 2 is formed. The dome-shaped casings 2b and 2c are dome-shaped optical members transparent to light, such as visible light, that is emitted by the illuminating units 3 and 6. The cylindrical casing 2a is a colored casing that is virtually not transparent to visible light. The cylindrical casing 2a has an outer diameter larger than those of the dome-shaped casings 2b and 2c, so that the dome-shaped casings can be fitted to the inner periphery of the cylindrical casing 2a near the openings on both ends. The capsule-shaped casing 2 that includes the cylindrical casing 2a and the dome-shaped casings 2b and 2c houses therein each unit of the capsule medical apparatus 1 in a watertight manner as illustrated in FIGS. 1 and 2.

The illuminating unit 3 illuminates an object of the solid-state imaging device 5. The illuminating unit 3 includes a plurality of light emitters 3a. The light emitters 3a are functional parts that are light emitting devices, such as LEDs, and mounted on the flexible board 13a. The light emitters 3a emit illumination light, such as white light, to an object (for example, the interior of the internal organs of the subject) on the F1-direction side through the dome-shaped casing 2b to illuminate the object on the F1-direction side, i.e., an object of the solid-state imaging device 5. A circuit for achieving the functions of the light emitters 3a is formed on the flexible board 13a and the flexible board 13a is attached on the rigid board 3b. In other words, the light emitters 3a are mounted on the rigid board 3b with the flexible board 13a interposed in between.

The optical system 4 is a functional part for forming an image of the object that is illuminated by the light emitters 3a. The optical system 4 includes lenses 4a and 4b; an aperture 4c that is arranged between the lenses 4a and 4b; and a lens frame 4d that holds the lenses 4a and 4b and the aperture 4c. The lenses 4a and 4b focus the light reflected from the object, which is illuminated by the light emitters 3a, on the F1-direction side, so that an image of the object on the F1-direction side is formed on the light receiving surface of the solid-state imaging device 5. The aperture 4c reduces (adjusts) the amount of reflected light, which is focused by the lenses 4a and 4b, to a preferable one. The lens frame 4d is a cylindrical frame with its ends open. The lens frame 4d holds the lens 4a on the inner upper end of the cylinder and holds the lens 4b on the inner lower end of the cylinder, and holds the aperture 4c between the lenses 4a and 4b. The lens frame 4d is fixed to the rigid board 3b in a way that the lens frame 4d is inserted into an opening that is formed at approximately the center of the rigid board 3b. In this case, the upper end (on the side of the lens 4a) of the lens frame 4d protrudes from the rigid board 3b and the flexible board 13a and is opposed to the dome-shaped casing 2b. It is preferable that the optical axes of the lenses 4a and 4b, which are held by the lens frame 4d, match the long axis CL that is the center axis of the capsule-shaped casing 2 in the longitudinal direction.

The solid-state imaging device 5 is a functional part for taking an image of the object that is illuminated by the light emitters 3a. The solid-state imaging device 5 is a semiconductor device such as a CCD or a CMOS. Specifically, the solid-state imaging device 5 is mounted on the flexible board 13b by, for example, flip-chip mounting. The solid-state imaging device 5 contacts with a leg of the lens 4b of the optical system 4. The light receiving surface of the solid-state imaging device 5 is opposed to the lens 4b. The solid-state imaging device 5 receives the light reflected from the object and focused by the lenses 4a and 4b of the optical system 4 through its light receiving surface and performs photoelectric conversion on the reflected light to take an in-vivo image of the object, i.e., the in-vivo image of the subject (the in-vivo image on the F1-direction side). A circuit for achieving the functions of the solid-state imaging device 5 is formed on the flexible board 13b on which the solid-state imaging device 5 is mounted.

The illuminating unit 6 illuminates an object of the solid-state imaging device 8. The illuminating unit 6 includes a plurality of light emitters 6a. The light emitters 6a are functional parts that are light emitting devices, such as LEDs, and mounted on the flexible board 13f. The light emitters 6a emit illumination light, such as white light, to an object (for example, the interior of the internal organs of the subject) on the F2-direction side through the dome-shaped casing 2c to illuminate the object on the F2-direction side, i.e., an object of the solid-state imaging device 8. A circuit for achieving the functions of the light emitters 6a is formed on the flexible board 13f and the flexible board 13f is attached on the rigid board 6b. In other words, the light emitters 6a are mounted on the rigid board 6b with the flexible board 13f interposed in between.

The optical system 7 is a functional part for forming an image of the object that is illuminated by the light emitters 6a. The optical system 7 includes lenses 7a and 7b; an aperture 7c that is arranged between the lenses 7a and 7b; and a lens frame 7d that holds the lenses 7a and 7b and the aperture 7c. The lenses 7a and 7b focus the light reflected from the object, which is illuminated by the light emitters 6a, on the F2-direction side, so that an image of the object on the F2-direction side is formed on the light receiving surface of the solid-state imaging device 8. The aperture 7c reduces (adjusts) the amount of reflected light, which is focused by the lenses 7a and 7b, to a preferable one. The lens frame 7d is a cylindrical frame with its ends open. The lens frame 7d holds the lens 7a on the inner upper end of the cylinder and holds the lens 7b on the inner lower end of the cylinder, and holds the aperture 7c between the lenses 7a and 7b. The lens frame 7d is fixed to the rigid board 6b in a way that the lens frame 7d is inserted into an opening that is formed at approximately the center of the rigid board 6b. In this case, the upper end (on the side of the lens 7a) of the lens frame 7d protrudes from the rigid board 6b and the flexible board 13f and is opposed to the dome-shaped casing 2c. It is preferable that the optical axes of the lenses 7a and 7b, which are held by the lens frame 7d, match the long axis CL of the capsule-shaped casing 2.

The solid-state imaging device 8 is a functional part for taking an image of the object that is illuminated by the light emitters 6a. The solid-state imaging device 5 is a semiconductor device such as a CCD or a CMOS. Specifically, the solid-state imaging device 8 is mounted on the flexible board 13e by, for example, flip-chip mounting. The solid-state imaging device 8 contacts with a leg of the lens 7b of the optical system 7. The light receiving surface of the solid-state imaging device 8 is opposed to the lens 7b. The solid-state imaging device 8 receives the light reflected from the object and focused by the lenses 7a and 7b of the optical system 7 through its light receiving surface and performs photoelectric conversion on the reflected light to take an in-vivo image of the object, i.e., the in-vivo image of the subject (the in-vivo image on the F2-direction side). A circuit for achieving the functions of the solid-state imaging device 8 is formed on the flexible board 13e on which the solid-state imaging device 8 is mounted.

The wireless communication unit 9 wirelessly transmits each in-vivo image that is taken by the solid-state imaging device 5 or the solid-state imaging device 8 to the receiving apparatus (not shown) outside the subject. The wireless communication unit 9 includes a communication processor 9a that is electrically connected to an antenna 9b. The communication processor 9a is a functional part that wirelessly transmits an image signal through the antenna 9b and mounted on the rigid board 9c. The communication processor 9a receives an image signal of each in-vivo image, which is taken by the solid-state imaging device 5 or the solid-state imaging device 8, from the control unit 10. The communication processor 9a generates a wireless signal of each in-vivo image by performing a communication process, such as modulation, on an image signal of each in-vivo image, and sequentially transmits a wireless signal of each in-vivo image through the antenna 9b. As illustrated in FIGS. 1 and 2, the antenna 9b is mounted on the flexible board 13f and connected to the communication processor 9a through the flexible boards 13d, 13e, and 13f and the rigid board 9c.

The control unit 10 is a functional part for controlling the units of the capsule medical apparatus 1 and mounted on the flexible board 13d. The control unit 10 includes a CPU that executes process programs, a ROM that stores various types of data, and a RAM that temporarily stores computation parameters. The control unit 10 controls the operation of the units, i.e., the illuminating units 3 and 6, the solid-state imaging devices 5 and 8, and the wireless communication unit 9, and controls input/output of signals between these units. The control unit 10 has various parameters about image processing, such as white balance, and has an image processing function of sequentially generating an image signal that contains an in-vivo image on the F1-direction side, which is taken by the solid-state imaging device 5, and an image signal that contains an in-vivo image on the F2-direction side, which is taken by the solid-state imaging device 8. The control unit 10 controls the communication processor 9a to wirelessly transmit an in-vivo image on the F1-direction side and an in-vivo image on the F2-direction side alternately.

A circuit for achieving the functions of the control unit 10 is formed on the flexible board 13d, on which the control unit 10 is mounted. The flexible board 13d is attached to the rigid board 9c. In other words, the communication processor 9a is mounted on the rigid board 9c, and the control unit 10 is mounted on the rigid board 9c with the flexible board 13d interposed in between.

The power supply controller 11 is a functional part for switching on/off the power supply of the capsule medical apparatus 1 and mounted on the rigid board 11b. The power supply controller 11 includes a regulator and a magnetic switch 11a and controls supply of electric power to the functional parts of the capsule medical apparatus 1. The magnetic switch 11a switches between the on and off states with a magnetic field that is externally applied. When the magnetic switch 11a is on, electric power from the batteries 12a and 12b is appropriately supplied to the functional parts of the capsule medical apparatus 1. When the magnetic switch 11a is off, supply of electric power to the functional parts of the capsule medical apparatus 1 is stopped.

A circuit for achieving the functions of the power supply controller 11 is formed on the rigid board 11b on which the power supply controller 11 is mounted, and the flexible board 13c is connected to the rigid board 11b. The power supply controller 11 is connected to the functional parts of the capsule medical apparatus 1 through the rigid board 11b and the flexible board 13c.

The batteries 12a and 12b are button batteries, such as silver oxide batteries, and stores therein electric power necessary for the operation of the functional parts of the capsule medical apparatus 1. The batteries 12a and 12b are electrically connected to the power supply controller 11 through a contact spring (not shown) and supplies electric power to the functional parts of the capsule medical apparatus 1 based on the control of the power supply controller 11 as described above. The number of batteries that are incorporated as power supply of the capsule medical apparatus 1 is not limited to two as long as necessary electric power can be supplied to the functional parts.

The rigid boards 3b, 6b, 9c, and 11b and the flexible boards 13a to 13f, on which the functional parts, such as the illuminating units 3 and 6 and the solid-state imaging devices 5 and 8 are mounted, correspond to a series of circuit boards that are incorporated in the capsule medical apparatus 1. Specifically, in the series of circuit boards, the flexible board 13a is connected to the flexible board 13b, and the flexible board 13b is connected to the rigid board 11b through the flexible board 13c. The flexible board 13f is connected to the flexible board 13e, and the flexible board 13e is connected to the rigid board 9c through the flexible board 13d. The flexible board 13d is connected to the rigid board 11b through the flexible board 13c. The rigid board 9c is a circular board from which a part on the circumference is cut in a D shape. Internal parts, such as the flexible board 13d, are arranged in the space between the part from which a part is cut in a D shape and the inner wall of the cylindrical casing 2a. The structures of the rigid boards 3b, 6b, and 11b are similar to that of the rigid board 9c.

The series of circuit boards on which the functional parts are mounted are used to assemble internal parts 15 that are incorporated in the capsule medical apparatus 1. The rigid boards 3b, 6b, 9c, and 11b and the flexible boards 13a to 13f, which are included in the internal parts 15 of the capsule medical apparatus 1, are arranged with their surfaces opposed as illustrated in FIGS. 1 and 2.

The part holders 16 and 17 function as board separating members that keeps the rigid boards 3b, 6b, 9c, and 11b that are included in the internal parts 15 of the capsule medical apparatus 1 separated. Specifically, the part holders 16 and 17 have a cylindrical structure or a frame structure along the arc-shaped circumference of each of the rigid boards 3b, 6b, 9c, and 11b. A plurality of fitting portions 16a to 16d to which the rigid boards 3b, 11b, 9c, and 6b are fitted respectively are formed on the inner wall of the part holder 16. Similarly, a plurality of fitting portions 17a to 17d to which the rigid boards 3b, 11b, 9c, and 6b are fitted respectively are formed on the inner wall of the part holder 17. Each of the fitting portions 16a to 16d and the fitting portions 17a to 17d is formed in a concave shape such that the circumference of a rigid board (specifically, any one of the rigid boards 3b, 11b, 9c, and 6b) of the internal parts 15 can be fitted to the fitting portion. Engaging portions 16e, 16f, 17e, and 17f that protrude inward such that the engaging portions 16e and 16f are opposed respectively to the engaging portions 17e and 17f are formed on the inner walls of the part holders 16 and 17. The engaging portion 16e of the part holder 16 and the engaging portion 17e of the part holder 17 from the engaging portions 16e, 16f, 17e, and 17f are engaged with each other, and the engaging portion 16f of the part holder 16 and the engaging portion 17f of the part holder 17 are engaged with each other.

In the part holders 16 and 17 having the above structure, the engaging portions 16e, 16f, 17e, and 17f are engaged with each other and integrated and the rigid boards 3b, 11b, 9c, and 6b are fitted sideways to the fitting portions 16a to 16d and 17a to 17d. Accordingly, the part holders 16 and 17 sandwich the rigid boards 3b, 11b, 9c, and 6b of the internal parts 15, so that the rigid boards 3b, 11b, 9c, and 6b are kept separated. The batteries 12a and 12b are arranged between the engaging portions 16e and 17e and the engaging portions 16f and 17f of the part holders 16 and 17, which are integrated. The part holders 16 and 17 are a pair of members that correspond to integrated board-separation keeping units that keep the rigid boards 3b, 11b, 9c, and 6b of the internal parts 15 separated. The part holders 16 and 17 in a pair may be a plurality of members that are independently manufactured by a molding process, or may be a plurality of parts that are obtained by dividing an integrated board separating member along the long axis CL of the capsule medical apparatus 1.

Figure 4:
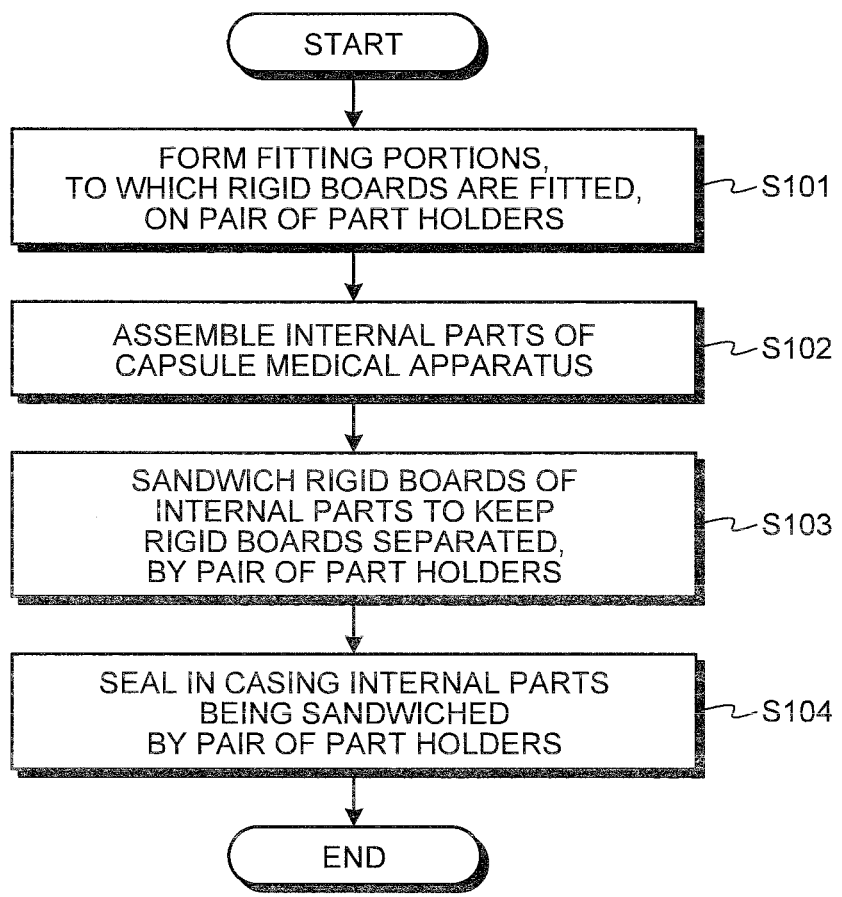
FIG. 4 is a flowchart that represents an example of a method of manufacturing the capsule medical apparatus according to the first embodiment of the present invention.
Figure 5:
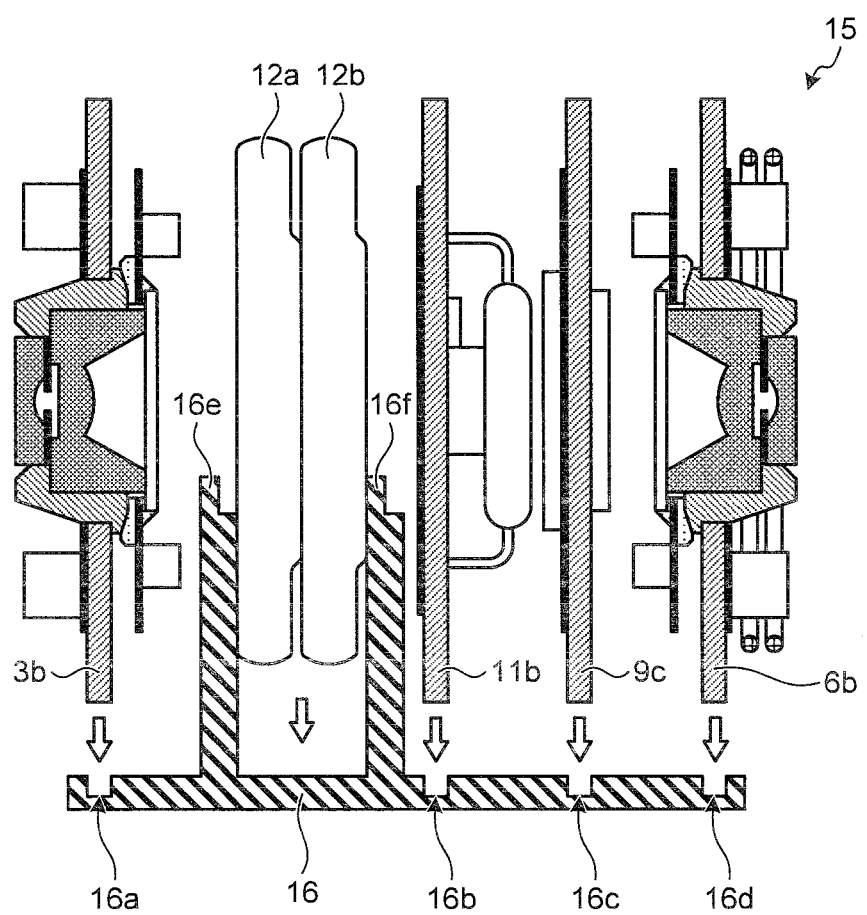
FIG. 5 is a schematic diagram exemplarily representing that internal parts of the capsule medical apparatus are fitted to one of a pair of part holders.
Figure 6:
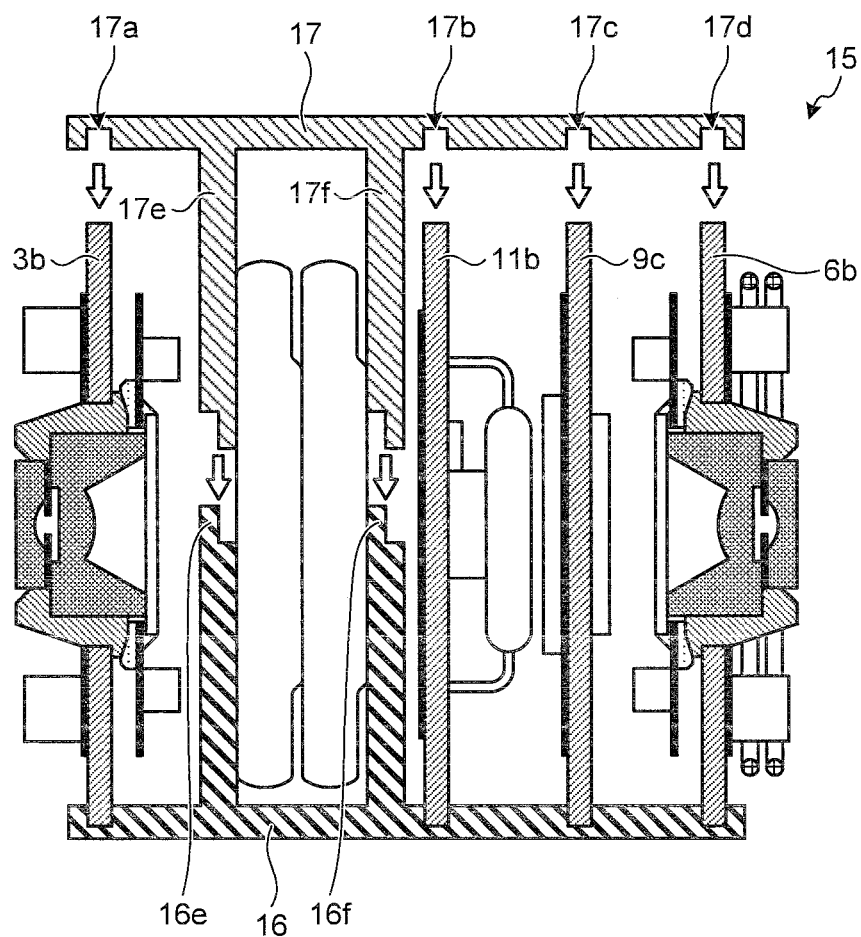
FIG. 6 is a schematic diagram exemplarily representing that the internal parts of the capsule medical apparatus are sandwiched by the part holders in a pair.
Figure 7:
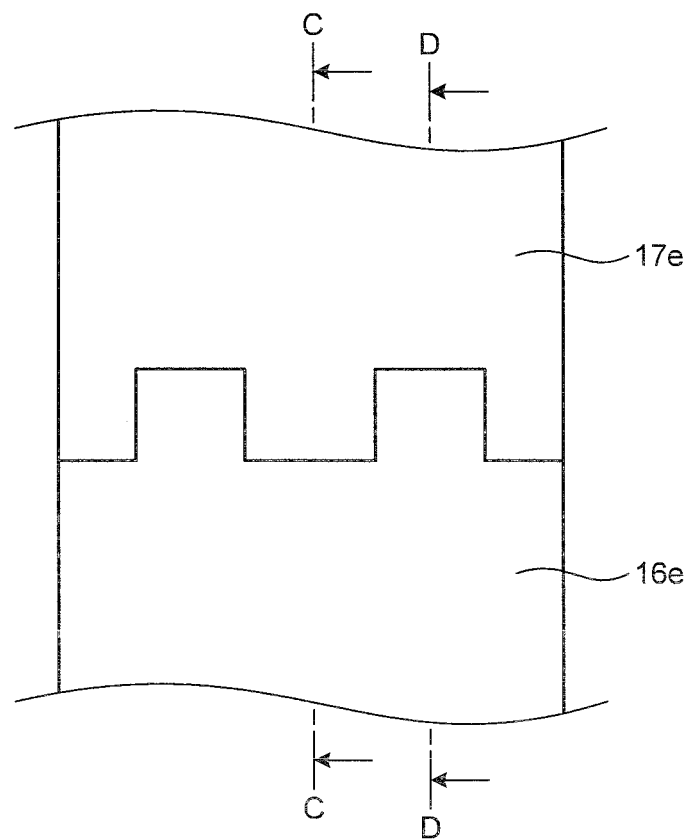
FIG. 7 is a schematic diagram exemplarily representing that engaging portions of the part holders in a pair are engaged.
Figure 8A:
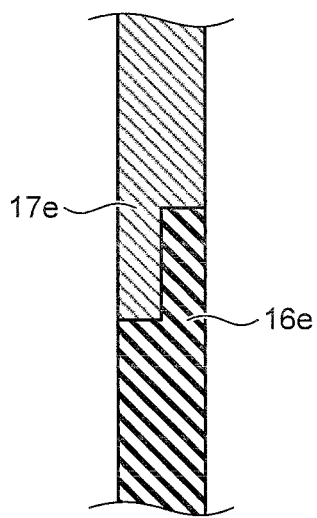
FIG. 8A is a schematic cross-sectional view, taken along C-C line, of the engaging portions represented in FIG. 7.
Figure 8B:
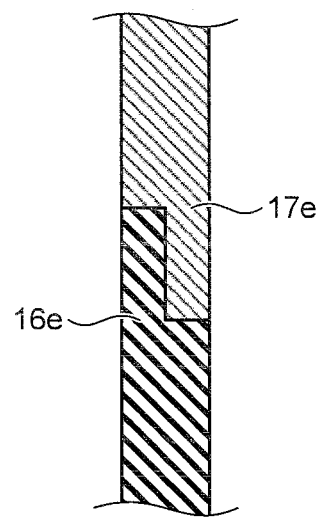
FIG. 8B is a schematic cross-sectional view, taken along D-D line, of the engaging portions represented in FIG. 7.

A method of manufacturing the capsule medical apparatus 1 according to the first embodiment of the present invention will be explained. FIG. 4 is a flowchart that represents an example of the method of manufacturing the capsule medical apparatus according to the first embodiment of the present invention. FIG. 5 is a schematic diagram exemplarily representing that internal parts of the capsule medical apparatus are fitted to one of the part holders in a pair. FIG. 6 is a schematic diagram exemplarily representing that internal parts of the capsule medical apparatus are sandwiched by the part holders in a pair. FIG. 7 is a schematic diagram exemplarily representing that the engaging portions of the part holders in a pair are engaged. FIG. 8A is a schematic cross-sectional view, taken along line C-C, of the engaging portions illustrated in FIG. 7. FIG. 8B is a schematic cross-sectional view, taken along line D-D, of the engaging portions illustrated in FIG. 7. FIG. 9 is a schematic diagram representing that the internal parts that are sandwiched by the part holders in a pair are housed in the capsule-shaped casing.

As represented in FIG. 4, the fitting portions 16a to 16d and 17a to 17d to which the rigid boards 3b, 11b, 9c, and 6b are fitted are formed in the inner walls of the part holders 16 and 17 in a pair (step S101). At step S101, the fitting portions 16a to 16d may be formed together with the part holder 16 in forming process of the part holder 16, or may be formed by cutting the wall surface of the part holder 16 after the part holder 16 is formed. Similarly, the fitting portions 17a to 17d may be formed together with the part holder 17 in forming process of the part holder 17, or may be formed by cutting the wall surface of the part holder 17 after the part holder 17 is formed.

The fitting portions 16a to 16d and 17a to 17d may be formed on the inner wall of a board-separation keeping unit that is integrally formed by forming process. In this case, the integrated board-separation keeping unit that has the fitting portions 16a to 16d and 17a to 17d on its inner wall is divided into the part holder 16 having the fitting portions 16a to 16d and the part holder 17 including the fitting portions 17a to 17d along the long axis CL of the capsule medical apparatus 1.

Subsequently, the internal parts 15 that are incorporated in the capsule medical apparatus 1 are assembled (step S102). At Step S102, the functional parts including the light emitters 3a and 6a, the optical systems 4 and 7, the solid-state imaging devices 5 and 8, the communication processor 9a, the control unit 10, and the power supply controller 11 are appropriately mounted on the rigid boards 3b, 6b, 9c, and 11b and the flexible boards 13a to 13f. The series of circuit boards that are formed by connecting the rigid boards 3b, 6b, 9c, and 11b and the flexible boards 13a to 13f, on which the functional parts are mounted, and the batteries 12a and 12b are combined to assemble the internal parts 15 of the capsule medical apparatus 1.

The rigid boards 3b, 6b, 9c, and 11b and the flexible boards 13a to 13f of the internal parts 15, which are assembled as described above, are arranged with their board surfaces opposed as illustrated in FIGS. 1 and 2. For example, the batteries 12a and 12b are arranged between the rigid boards 3b and 11b of the internal parts 15.

Subsequently, the rigid boards 3b, 6b, 9c, and 11b of the internal parts 15 are sandwiched by the part holders 16 and 17 in a pair, in which the fitting portions 16a to 16d and 17a to 17d are formed at step S101, to keep the rigid boards 3b, 6b, 9c, and 11b separated (step S103). At step S103, the internal parts 15 are fitted to one of the part holders 16 and 17 in a pair. Thereafter, one of the part holders 16 and 17 in a pair is fitted to the internal parts 15 to sandwich the internal parts 15 between the part holders 16 and 17 in a pair.

Specifically, the internal parts 15 are fixed to the part holder 16 out of the part holders 16 and 17 in a pair as illustrated in FIG. 5. In this case, the circumference of the rigid board 3b of the internal parts 15 is fitted sideways to the fitting portion 16a, the circumference of the rigid board 11b is fitted sideways to the fitting portion 16b, the circumference of the rigid board 9c is fitted to the fitting portion 16c, and the circumference of the rigid board 6b is fitted to the fitting portion 16d. The part holder 16 supports the internal parts 15 with the rigid boards 3b, 11b, 9c, and 6b fitted respectively to the fitting portions 16a to 16d. The batteries 12a and 12b of the internal parts 15 are arranged between the engaging portions 16e and 16f of the part holder 16.

After the internal parts 15 are fixed to the part holder 16, the part holder 17 out of the part holders 16 and 17 in a pair is fixed to the internal parts 15 as illustrated in FIG. 6. In this case, while the engaging portions 17e and 17f of the part holder 17 are gradually engaged with the engaging portions 16e and 16f of the part holder 16, to which the internal parts 15 are already fixed, the fitting portions 17a to 17d are fitted respectively to the rigid boards 3b, 11b, 9c and 6b of the internal parts 15. More specifically, the circumference of the rigid board 3b is fitted sideways to the fitting portion 17a, the circumference of the rigid board 11b is fitted sideways to the fitting portion 17b, the circumference of the rigid board 9c is fitted sideways to the fitting portion 17c, and the circumference of the rigid board 6b is fitted sideways to the fitting portion 17d.

The engaging portions 16e and 17e of the part holders 16 and 17 in a pair have, for example, a plurality of (for example, three) concave and convex portions that can be engaged with each other as illustrated in FIGS. 7 and 8. The engaging portions 16e and 17e are engaged with the concave and convex portions engaged with each other. The structures of the engaging portions 16f and 17f of the part holders 16 and 17 in a pair are similar to those of the engaging portions 16e and 17e.

In the state where the engaging portions 16e and 17e are engaged with each other and the engaging portions 16f and 17f are engaged with each other, the part holders 16 and 17 in a pair fit the rigid boards 3b, 11b, 9c, and 6b of the internal parts 15 to the fitting portions 16a to 16d and 17a to 17d. As described above, the part holders 16 and 17 in a pair sandwich the internal parts 15 between the rigid boards 3b, 11b, 9c, and 6b and sandwich the rigid boards 3b, 11b, 9c, and 6b, so that the rigid boards 3b, 11b, 9c, and 6b are kept separated.

Thereafter, the internal parts 15 that are sandwiched by the part holders 16 and 17 in a pair are sealed in the capsule-shaped casing 2, which is the casing of the capsule medical apparatus 1 (step S104), and manufacturing the capsule medical apparatus 1 is completed.

At step S104, as illustrated in FIG. 9, the internal parts 15 that are sandwiched by the part holders 16 and 17 in a pair are housed in the cylindrical casing 2a, which is the body of the capsule-shaped casing 2. Thereafter, the dome-shaped casings 2b and 2c are fitted to the openings on both sides of the cylindrical casing 2a, so that the openings on both sides of the cylindrical casing 2a are closed in a watertight manner. As a result, the internal parts 15 are sealed in the capsule-shaped casing 2 with the boards separated by the part holders 16 and 17. Both ends of the part holders 16 and 17 are pressed against the ends of the dome-shaped casings 2b and 2c in the capsule-shaped casing 2, so that the internal parts 15 are positioned in the space in the capsule-shaped casing 2.

In the method of manufacturing the capsule medical apparatus 1, the step of assembling the internal parts 15 (step S102) may be performed prior to the step of forming the fitting portions 16a to 16d and 17a to 17d in the part holders 16 and 17 in a pair (step S101).

As described above, in the capsule medical apparatus and the method of manufacturing the capsule medical apparatus according to the first embodiment of the present invention, the rigid boards, on which the functional parts are mounted, are sandwiched by a pair of part holders in a pair to keep the rigid boards separated from each other. Therefore, without forming a multi-layered structure in which ring-shaped board separating members or frame separating members to keep board separated and rigid boards are alternately superposed, the rigid boards whose surfaces are opposed are fixed sideways to the part holders, so that the rigid boards can be easily kept separated. Therefore, even a capsule medical apparatus that incorporates a plurality of rigid boards can be easily manufactured.

In addition, the rigid boards are collectively sandwiched by a predetermined number of (for example, a pair of) part holders. Thus, the predetermined number of part holders can keep the rigid boards separated, regardless the number of intervals between the rigid boards to be incorporated. This reduces the number of members necessary for manufacturing the capsule medical apparatus.

When the rigid boards are sandwiched by the part holders in a pair, it suffices that at least a part of the circumference of each rigid board is supported by the member supporter, and it is not necessary to fix the entire circumference of each rigid board to the part holder. Thus, the cylindrical structure or the frame structure can be thin and small as much as possible, which further reduces the weight of the capsule medical apparatus.

Second Embodiment

A second embodiment of the present invention will be explained. In the first embodiment, the part holders 16 and 17, which are different from the capsule-shaped casing 2, keeps the boards of the internal parts 15 separated. In the second embodiment, a capsule-shaped casing that incorporates therein a plurality of rigid boards has a function of board-separation keeping units that keep the rigid boards separated.

Figure 10:
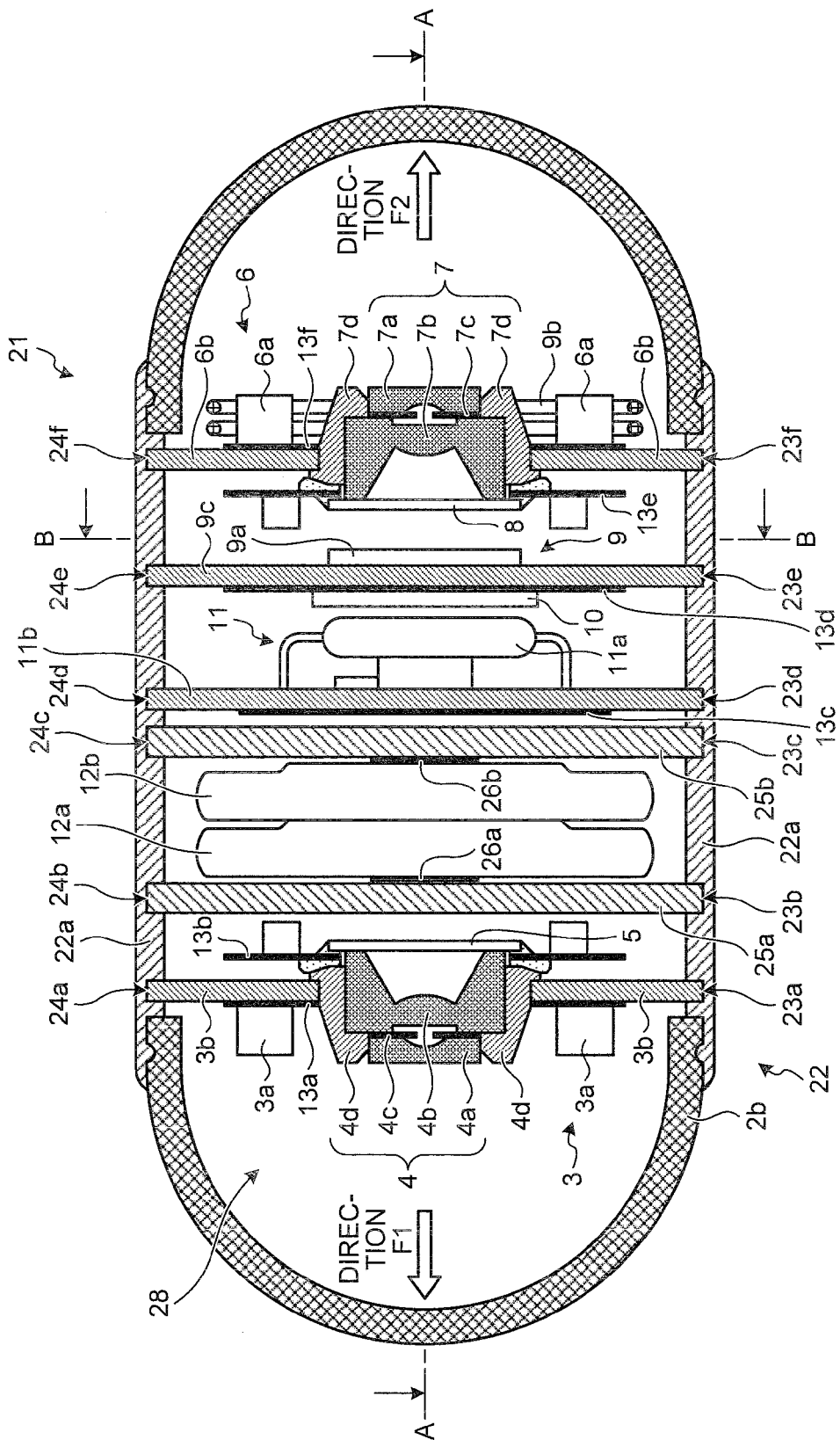
FIG. 10 is a schematic cross-sectional view that represents a configuration example of a capsule medical apparatus according to a second embodiment of the present invention.
Figure 11:
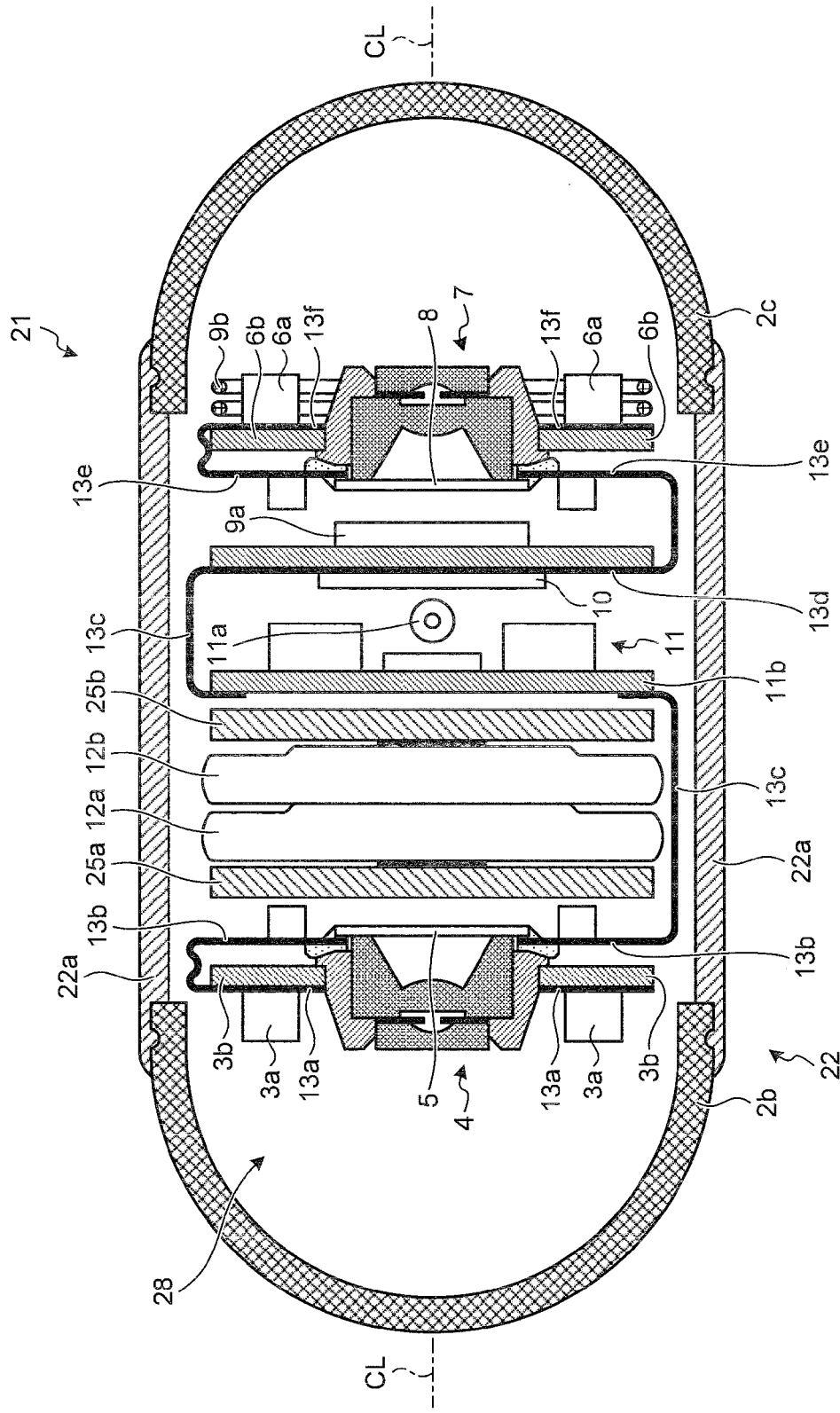
FIG. 11 is a schematic cross-sectional view, taken along A-A line, of the capsule medical apparatus illustrated in FIG. 10.
Figure 12:
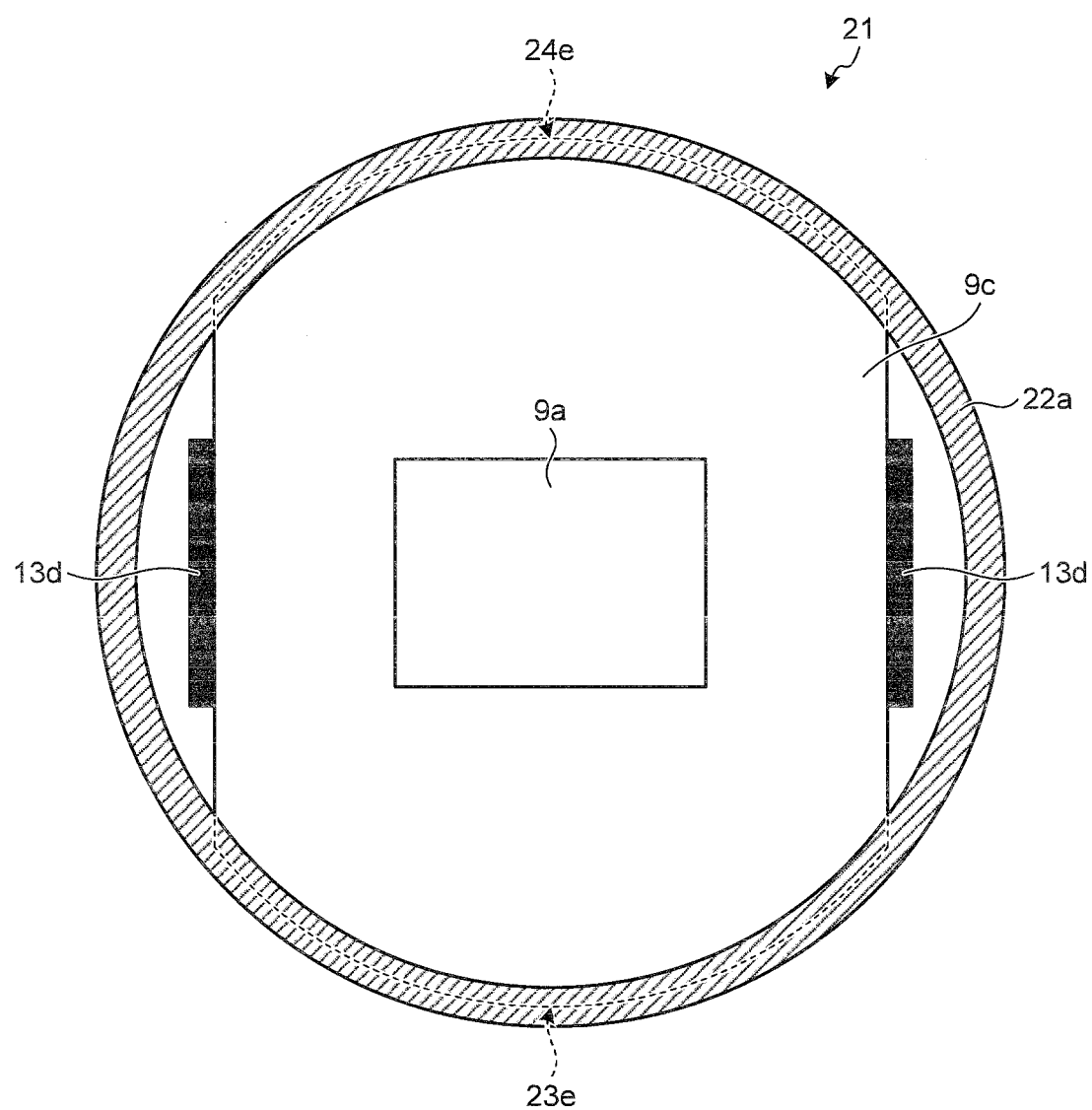
FIG. 12 is a schematic cross-sectional view, taken along B-B line, of the capsule medical apparatus illustrated in FIG. 10.

FIG. 10 is a schematic cross-sectional view that represents a configuration example of a capsule medical apparatus according to the second embodiment of the present invention. FIG. 11 is a schematic cross-sectional view, taken along A-A line, of the capsule medical apparatus illustrated in FIG. 10. FIG. 12 is a schematic cross-sectional view, taken along B-B line, of the capsule medical apparatus illustrated in FIG. 10. As illustrated in FIGS. 10 to 12, a capsule medical apparatus 21 according to the second embodiment includes a capsule-shaped casing 22, which has a board-separation keeping function, instead of the capsule-shaped casing 2 and the part holders 16 and 17 of the capsule medical apparatus 1 according to the first embodiment. The capsule-shaped casing 22 includes a cylindrical casing 22a instead of the cylindrical casing 2a of the capsule medical apparatus 1 according to the first embodiment. The capsule medical apparatus 21 includes rigid boards 25a and 25b that support the batteries 12a and 12b. The rigid boards 25a and 25b are respectively provided with contact springs 26a and 26b for electrically connecting the rigid boards 25a and 25b to the batteries 12a and 12b. Other aspects of the configuration are the same as those of the first embodiment, and the same elements are denoted by the same reference numerals.

The capsule-shaped casing 22 includes as its body the cylindrical casing 22a that has a function of the board-separation keeping units. The edges of openings of the cylindrical casing 22a on both sides are closed with the dome-shaped casings 2b and 2c. The capsule-shaped casing 22 is similar to the capsule-shaped casing 2 of the capsule medical apparatus 1 according to the first embodiment, except for the structure and functions of the cylindrical casing 22a.

The cylindrical casing 22a has a function of a part (body) of the capsule-shaped casing 22 and a function of the board-separation keeping units. Specifically, fitting portions 23a and 24a that are fitted to the rigid board 3b; fitting portions 23b and 24b that are fitted to the rigid board 25a; fitting portions 23c and 24c that are fitted to the rigid board 25b; fitting portions 23d and 24d that are fitted to the rigid board 11b; fitting portions 23e and 24e that are fitted to the rigid board 9c; and fitting portions 23f and 24f that are fitted to the rigid board 6b, are formed on the inner wall of the cylindrical casing 22a. The fitting portions 23a to 23f and the fitting portions 24a to 24f are each formed in a concave shape such that the circumference of an incorporated board (specifically, any one of the rigid boards 3b, 25a, 25b, 11b, 9c, and 6b) can be fitted to the fitting portion.

Figure 13:
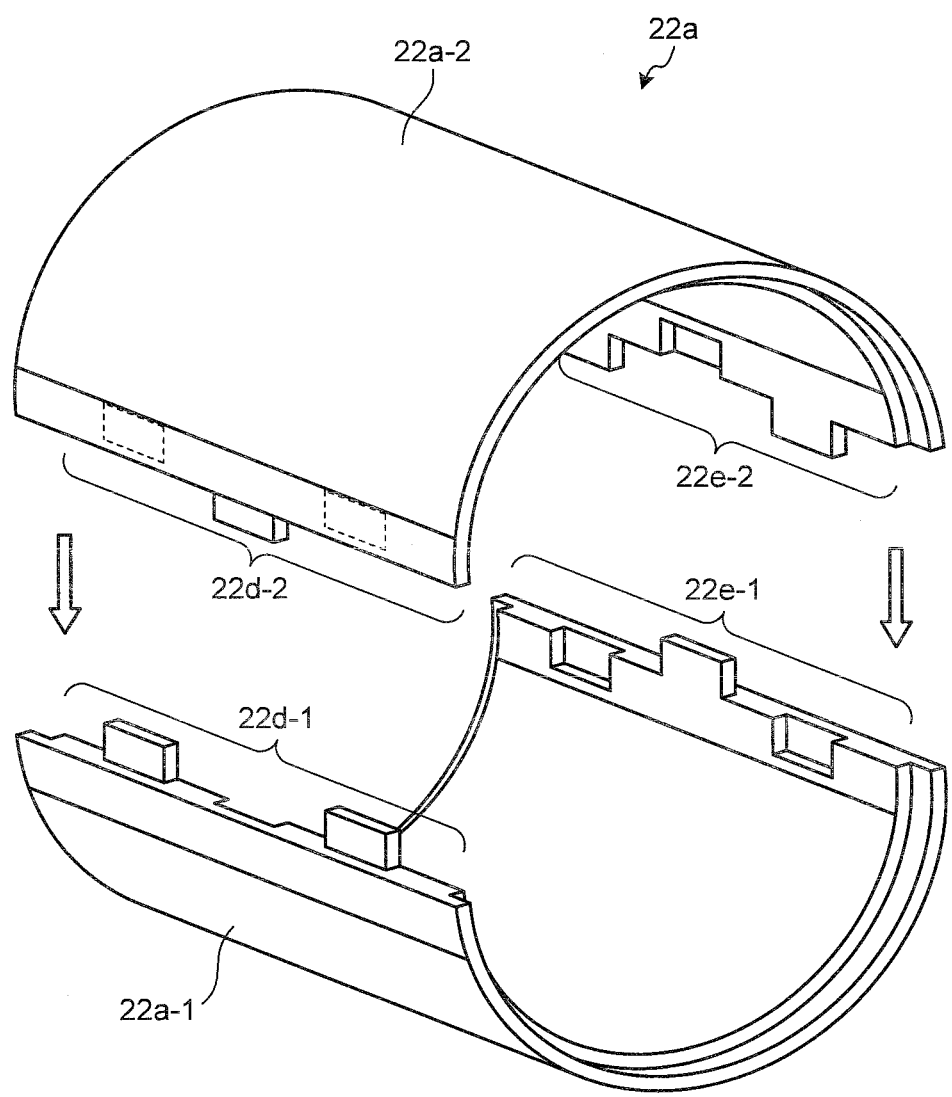
FIG. 13 is a schematic diagram representing that a cylindrical casing, which is the body of a capsule-shaped casing, is divided along a long axis of the capsule-shaped casing.

The cylindrical casing 22a is an integrated casing formed by combining a plurality of members. FIG. 13 is a schematic diagram representing that the cylindrical casing, which is the body of the capsule-shaped casing, is divided along the long axis of the capsule-shaped casing. As illustrated in FIG. 13, the cylindrical casing 22a is divided into a pair of divided parts 22a-1 and 22a-2. The divided parts 22a-1 and 22a-2 are obtained by dividing the cylindrical casing 22a into two parts along the long axis CL (see FIG. 11) of the capsule-shaped casing 22. Engaging portions 22d-1 and 22e-1 are formed on the ends of the divided part 22a-1. Engaging portions 22d-2 and 22e-2 are formed on the ends of the divided part 22a-2.

The engaging portions 22d-1 and 22d-2 are formed in concave and convex shapes such that the engaging portions 22d-1 and 22d-2 can be engaged with each other. The engaging portions 22e-1 and 22e-2 are formed in concave and convex shapes such that the engaging portions 22e-1 and 22e-2 can be engaged with each other. The divided parts 22a-1 and 22a-2 in a pair are firmly fixed to each other with the engaging portions 22d-1 and the engaging portions 22d-2 engaged with each other and the engaging portion 22e-1 and the engaging portion 22e-2 engaged with each other. Accordingly, the divided parts 22a-1 and 22a-2 do not relatively move in the direction of the long axis CL or radially and are integrated into the cylindrical casing 22a. Although it is not particularly illustrated in FIG. 13, the fitting portions 23a to 23f are formed on the inner wall of the divided part 22a-1, and the fitting portions 24a to 24f are formed on the inner wall of the divided part 22a-2.

The cylindrical casing 22a has a structure and functions similar to those of the cylindrical casing 2a of the capsule medical apparatus 1 according to the first embodiment except that the cylindrical casing 22a is formed by integrating the divided parts 22a-1 and 22a-2 as illustrated in FIG. 13 and has the function of the board-separation keeping units.

The series of circuit boards that are incorporated in the capsule medical apparatus 21 include the rigid boards 25a and 25b that support the batteries 12a and 12b, in addition to the rigid boards 3b, 6b, 9c, and 11b and the flexible boards 13a to 13f. The rigid boards 25a and 25b are provided with the contact springs 26a and 26b. The batteries 12a and 12b are electrically connected to the power supply controller 11 through the contact springs 26a and 26b and the rigid boards 25a and 25b. The rigid boards 25a and 25b are, for example, circular boards whose circumference is partly cut off in a D-shape as in the case of the rigid board 9c illustrated in FIG. 12.

The series of circuit boards including the rigid boards 25a and 25b are used to assemble internal parts 28 that are incorporated in the capsule medical apparatus 21. The rigid boards 3b, 6b, 9c, 11b, 25a, and 25b and the flexible boards 13a to 13f are arranged with their surfaces opposed as illustrated in FIGS. 10 and 11.

While the divided parts 22a-1 and 22a-2 in a pair that constitute the cylindrical casing 22a are integrated, with the engaging portions 22d-1 and 22d-2 engaged with each other and firmly fixed and the engaging portions 22e-1 and 22e-2 engaged with each other and firmly fixed as illustrated in FIG. 13, the rigid boards 3b, 25a, 25b, 11b, 9c, and 6b are fitted sideways to the fitting portions 23a to 23f and 24a to 24f. Accordingly, the divided parts 22a-1 and 22a-2 in a pair are integrated into the cylindrical casing 22a and sandwich the rigid boards 3b, 25a, 25b, 11b, 9c, and 6b of the internal parts 28 to keep the rigid boards 3b, 25a, 25b, 11b, 9c, and 6b separated. A part of the circumference of a rigid board (any one of the rigid boards 3b, 25a, 25b, 11b, 9c, and 6b) is fitted to each of the fitting portions 23a to 23f and 24a to 24f. For example, as illustrated in FIG. 12, the fitting portions 23e and 24e are fitted to a part of the circumference of the rigid board 9c (arc portions illustrated in FIG. 12).

Figure 14:
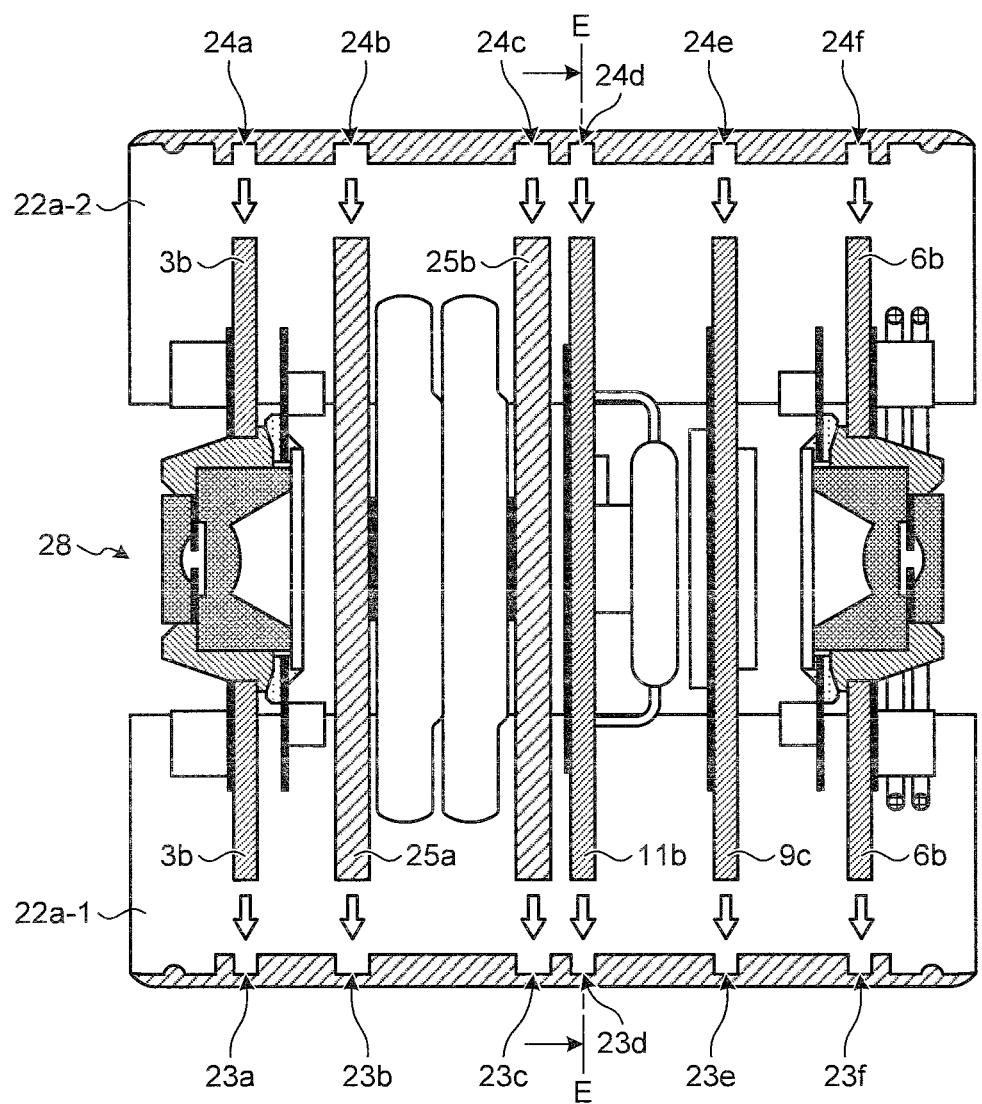
FIG. 14 is a schematic diagram representing that internal parts of the capsule medical apparatus are fitted by divided parts of the cylindrical casing.
Figure 15:
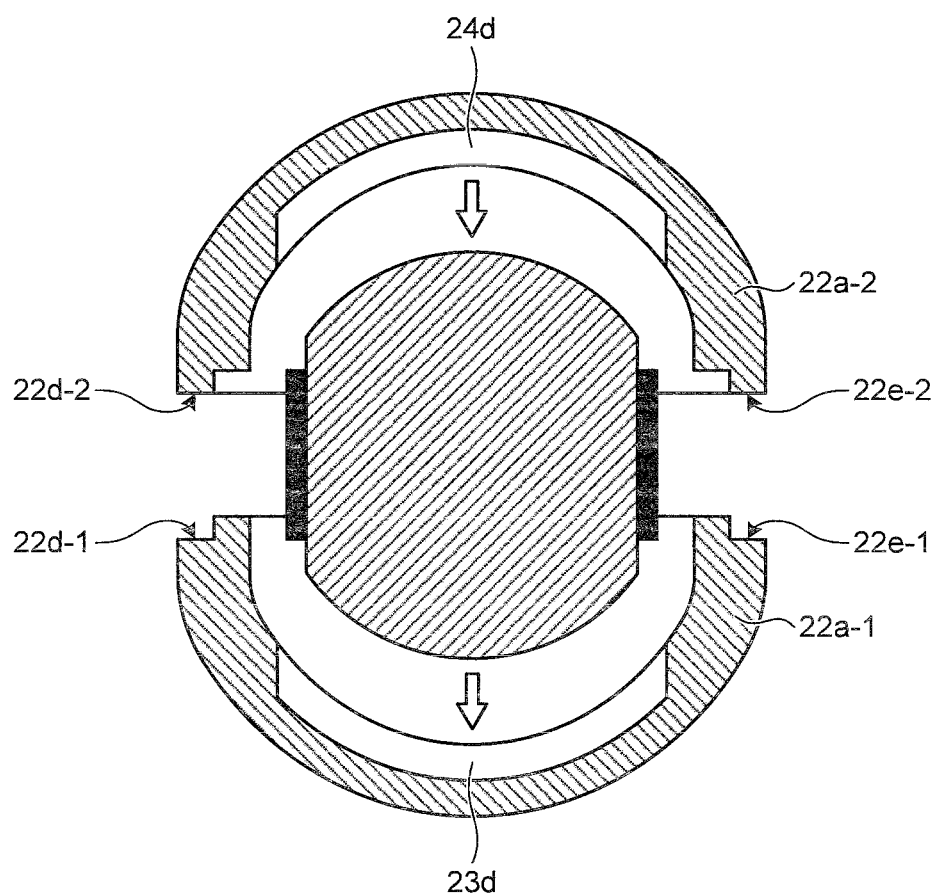
FIG. 15 is a schematic cross-sectional view, taken along E-E line, of the divided parts in a pair and the internal parts of the capsule medical apparatus illustrated in FIG. 14.

A method of manufacturing the capsule medical apparatus 21 according to the second embodiment of the present invention will be explained. FIG. 14 is a schematic diagram exemplarily representing that the divided parts of the cylindrical casing sandwich the internal parts of the capsule medical apparatus. FIG. 15 is a schematic cross-sectional view, taken along the E-E line, of the divided parts in a pair and the internal parts of the capsule medical apparatus illustrated in FIG. 14. The method of manufacturing the capsule medical apparatus 21 according to the second embodiment is approximately similar to steps S101 to S104 represented in FIG. 4, except that the divided parts 22a-1 and 22a-2 of the cylindrical casing 22a are used as a pair of part holders.

At step S101, the plurality of fitting portions 23a to 23f and 24a to 24f to which the rigid boards 3b, 25a, 25b, 11b, 9c, and 6b are fitted are formed on the inner walls of the divided parts 22a-1 and 22a-2 in a pair that forms the cylindrical casing 22a. The fitting portions 23a to 23f may be formed together with the divided part 22a-1 in forming process of the divided part 22a-1, or may be formed by cutting the wall surface of the divided part 22a-1 after the divided part 22a-1 is formed. Similarly, the fitting portions 24a to 24f may be formed together with the divided part 22a-2 in forming process of the divided part 22a-2, or may be formed by cutting the wall surface of the divided part 22a-2 after the divided part 22a-2 is formed. Alternatively, the fitting portions 23a to 23f and 24a to 24f may be formed in the inner wall of the cylindrical casing 22a that is integrally formed by forming process, and the cylindrical casing 22a may be then divided along the long axis CL of the capsule medical apparatus 21 into the divided part 22a-1 having the fitting portions 23a to 23f and the divided part 22a-2 having the fitting portions 24a to 24f.

At step S102, the internal parts 28 of the capsule medical apparatus 21 are assembled. The internal parts 28 of the capsule medical apparatus 21 are incorporated by electrically connecting the rigid boards 25a and 25b for supporting the batteries 12a and 12b to the rigid board 11b, and by combining the batteries 12a and 12b and the series of circuit boards that are formed by connecting the rigid boards 3b, 6b, 9c, 11b, 25a, and 25b and the flexible boards 13a to 13f.

The rigid boards 3b, 6b, 9c, 11b, 25a, and 25b and the flexible boards 13a to 13f of the internal parts 28 are arranged with their surfaces opposed as illustrated in FIGS. 10 and 11. The batteries 12a and 12b are sandwiched between the rigid boards 25a and 25b wile contacting with the contact springs 26a and 26b.

Subsequently, at step S103, the divided parts 22a-1 and 22a-2 in a pair, which form the cylindrical casing 22a, sandwich the rigid boards 3b, 6b, 9c, 11b, 25a, and 25b of the internal parts 28 to keep the rigid boards 3b, 6b, 9c, 11b, 25a, and 25b separated.

Specifically, as illustrated in FIG. 14, the internal parts 28 are fixed to the divided part 22a-1 out of the divided parts 22a-1 and 22a-2 in a pair, which form the cylindrical casing 22a. The circumference of the rigid board 3b of the internal parts 28 is fitted sideways to the fitting portion 23a, the circumference of the rigid board 25a is fitted sideways to the fitting portion 23b, and the circumference of the rigid board 25b is fitted sideways to the fitting portion 23c. Furthermore, the circumference of the rigid board 11b is fitted sideways to the fitting portion 23d, the circumference of the rigid board 9c is fitted sideways to the fitting portion 23e, and the circumference of the rigid board 6b is fitted sideways to the fitting portion 23f. The divided part 22a-1 supports the internal parts 28 with the rigid boards 3b, 25a, 25b, 11b, 9c, and 6b fitted respectively to the fitting portions 23a to 23f.

After the internal parts 28 are fixed to the divided part 22a-1, the divided part 22a-2 is fixed to the internal parts 28. As illustrated in FIG. 15, while the engaging portion 22d-1 of the divided part 22a-1 and the engaging portion 22d-2 of the divided part 22a-2 are engaged with each other and the engaging portion 22e-1 of the divided part 22a-1 and the engaging portion 22e-2 of the divided part 22a-2 are engaged with each other, the fitting portions 24a to 24f are fitted respectively to the rigid boards 3b, 25a, 25b, 11b, 9c, and 6b of the internal parts 28. More specifically, as illustrated in FIG. 14, the circumference of the rigid board 3b is fitted sideways to the fitting portion 24a, the circumference of the rigid board 25a is fitted sideways to the fitting portion 24b, and the circumference of the rigid board 25b is fitted sideways to the fitting portion 24c. Furthermore, the circumference of the rigid board 11b is fitted sideways to the fitting portion 24d, the circumference of the rigid board 9c is fitted sideways to the fitting portion 24e, and the circumference of the rigid board 6b is fitted sideways to the fitting portion 24f.

With the engaging portions 22d-1 and 22d-2 engaged with each other and the engaging portions 22e-1 and 22e-2 engaged with each other, the divided parts 22a-1 and 22a-2 in a pair fit the rigid boards 3b, 25a, 25b, 11b, 9c, and 6b of the internal parts 28 to the fitting portions 23a to 23f and 24a to 24f. In this manner, the divided parts 22a-1 and 22a-2 in a pair sandwich the internal parts 28 between the rigid boards 3b, 25a, 25b, 11b, 9c, and 6b and sandwich the rigid boards 3b, 25a, 25b, 11b, 9c, and 6b to keep the rigid boards 3b, 25a, 25b, 11b, 9c, and 6b separated.

The divided parts 22a-1 and 22a-2 are integrated, with the engaging portions 22d-1, 22d-2, 22e-1, and 22e-2 firmly fixed in a watertight manner, to the cylindrical casing 22a in which the boards are kept separated and the internal parts 28 are housed. In this case, the engaging portions 22d-1 and 22d-2 may be joined with each other and the engaging portions 22e-1 and 22e-2 may be joined with each other with an adhesive, or the engaging portions 22d-1 and 22d-2 may be welded and the engaging portions 22e-1 and 22e-2 may be welded by laser welding.

When the divided parts 22a-1 and 22a-2 are firmly fixed by laser welding, a laser is applied along the surfaces of the engaging portions 22d-1 and 22d-2 to be welded to weld the engaging portions 22d-1 and 22d-2. Similarly, a laser is applied along the surfaces of the engaging portions 22e-1 and 22e-2 to be welded to weld the engaging portions 22e-1 and 22e-2. A resin that contains a laser absorbent may be used to form the engaging portions 22d-1, 22d-2, 22e-1, and 22e-2 so that laser welding to weld the divided parts 22a-1 and 22a-2 can be easily performed.

Thereafter, at step S104, the internal parts 28 sandwiched in the cylindrical casing 22a, which is an integrated casing, are sealed in the capsule-shaped casing 22, which is the casing of the capsule medical apparatus 21. The dome-shaped casings 2b and 2c are fitted respectively to the edges of the openings on both sides of the cylindrical casing 22a, in which the internal parts 28 are housed and the boards are kept separated, so that the edges of the openings of the cylindrical casing 22a on both sides are closed in a watertight manner. As a result, the internal parts 28 are sealed in the capsule-shaped casing 22 with the boards kept separated by the cylindrical casing 22a.

As explained above, in the capsule medical apparatus and the method of manufacturing the capsule medical apparatus according to the second embodiment, the part holders in a pair that serve as a casing in which at least a plurality of rigid boards are housed, i.e., the divided parts in a pair forming the casing part having the board-separation keeping function, sandwich the rigid boards to keep the rigid boards separated. Other aspects of the configuration are similar to those the first embodiment. Thus, similar effects to those of the first embodiment can be achieved, and the rigid boards of the internal parts can be kept separated easily without a part holder different from the casing (outer casing) of the capsule medical apparatus. Accordingly, the number of parts necessary for manufacturing the capsule medical apparatus can be further reduced and the weight of the capsule medical apparatus can be further reduced.

Third Embodiment

A third embodiment of the present invention will be explained. In the second embodiment, the thickness of the area of the cylindrical casing 22a excluding the fitting portions 23a to 23f and 24a to 24f is larger than that of the fitting portions 23a to 23f and 24a to 24f. In the third embodiment, an area with the minimum thickness is formed in the casing area excluding the fitting portions 23a to 23f and 24a to 24f.

Figure 16:
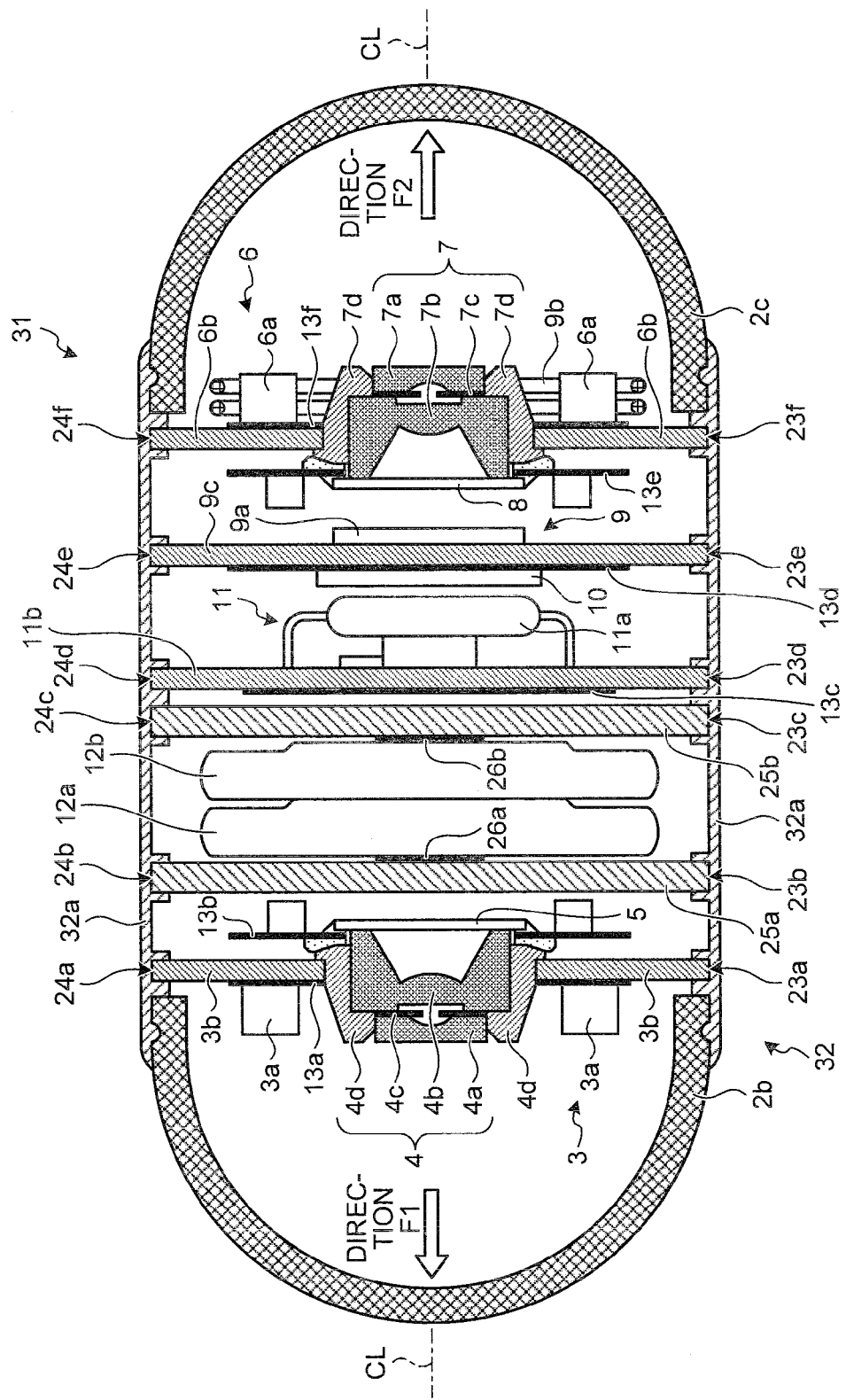
FIG. 16 is a schematic cross-sectional view that represents a configuration example of a capsule medical apparatus according to a third embodiment of the present invention.

FIG. 16 is a schematic cross-sectional view that represents a configuration example of a capsule medical apparatus according to the third embodiment of the present invention. As illustrated in FIG. 16, the capsule medical apparatus according to the third embodiment includes a capsule-shaped casing 32 instead of the capsule-shaped casing 22 of the capsule medical apparatus 21 according to the second embodiment. The capsule-shaped casing 32 includes a cylindrical casing 32a instead of the cylindrical casing 22a of the capsule medical apparatus 21 according to the second embodiment. Other aspects of the configuration are the same as those of the second embodiment, and the same elements are denoted by the same reference numerals.

The capsule-shaped casing 32 includes as its body the cylindrical casing 32a that has a board-separation keeping function similar to that of the cylindrical casing 22a of the second embodiment. The edges of openings of the cylindrical casing 32a on both sides are closed with the dome-shaped casings 2b and 2c. The capsule-shaped casing 32 is similar to the capsule-shaped casing 22 of the capsule medical apparatus 21 of the second embodiment except for the structure of the cylindrical casing 32a.

The cylindrical casing 32a is a cylindrical casing in which the thickness of the area of the cylindrical casing 22a excluding the fitting portions 23a to 23f and 24a to 24f is reduced as much as possible. Specifically, the area of the cylindrical casing 32a excluding the fitting portions 23a to 23f and 24a to 24f (hereinafter, "normal area") is formed in the minimum thickness of the cylindrical casing 32a. The minimum thickness is the smallest thickness necessary for assuring strength with which the outer shape of the cylindrical casing 32a can be maintained. If the thickness of the fitting portions 23a to 23f and 24a to 24f is the minimum thickness of the cylindrical casing 32a, the thickness of the normal area of the cylindrical casing 32a is reduced to the minimum thickness equal to that of the fitting portions 23a to 23f and 24a to 24f. In contrast, if the thickness of the fitting portions 23a to 23f and 24a to 24f is larger than the minimum thickness of the cylindrical casing 32a, the normal area of the cylindrical casing 32a is formed in a thickness smaller than that of the fitting portions 23a to 23f and 24a to 24f.

The cylindrical casing 32a is similar to the cylindrical casing 22a of the capsule medical apparatus 21 according to the second embodiment, except about the minimum thickness. In other words, a capsule medical apparatus 31 according to the third embodiment is similar to the capsule medical apparatus 21 according to the second embodiment, except about the minimum thickness of the cylindrical casing 32a. A method of manufacturing the capsule medical apparatus 31 is similar to the method of manufacturing the capsule medical apparatus according to the second embodiment.

It is preferable that the thickness of the overall normal area of the cylindrical casing 32a, excluding the fitting portions 23a to 23f and 24a to 24f, be small. Alternatively, a part of the normal area may have a small thickness. In other words, at least a part of the area of the cylindrical casing 32a excluding the fitting portions 23a to 23f and 24a to 24f may be a minimum-thickness area.

As explained above, in the third embodiment, the thickness of at least a part of the area of the cylindrical casing, which is the casing part having the board-separation keeping function, excluding the area of the fitting portions to be fitted to the rigid boards, is the minimum thickness of the cylindrical casing. Other aspects of the configuration are similar to those of the second embodiment. Therefore, similar effects to those of the second embodiment are achieved. In addition, the thickness of the cylindrical casing can be reduced to the required minimum thickness. As a result, the weight of the capsule medical apparatus can be further reduced.

Fourth Embodiment

A fourth embodiment of the present invention will be explained. In the second embodiment, the batteries 12a and 12b are sandwiched between the rigid boards 25a and 25b. In the fourth embodiment, the batteries 12a and 12b are sandwiched by the casing part opposed to side portions of the batteries 12a and 12b.

Figure 17:
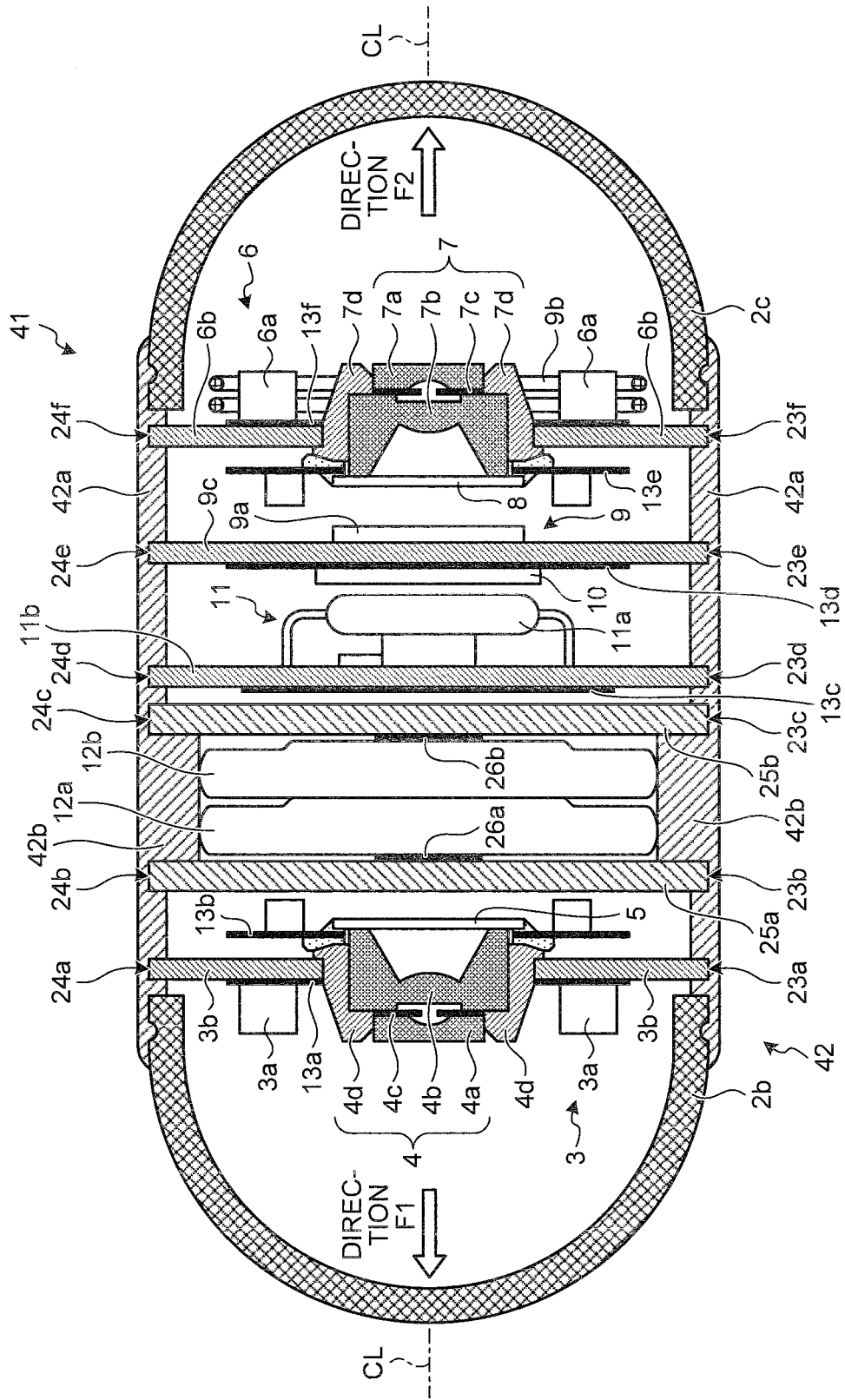
FIG. 17 is a schematic cross-sectional view that represents a configuration example of a capsule medical apparatus according to a fourth embodiment of the present invention.

FIG. 17 is a schematic cross-sectional view that represents a configuration example of a capsule medical apparatus according to the fourth embodiment of the present invention. As illustrated in FIG. 17, a capsule medical apparatus 41 according to the fourth embodiment includes a capsule-shaped casing 42 instead of the capsule-shaped casing 22 of the capsule medical apparatus 21 according to the second embodiment. The capsule-shaped casing 42 includes a cylindrical casing 42a instead of the cylindrical casing 22a of the capsule medical apparatus 21 according to the second embodiment. Other aspects of the configuration are the same as those of the second embodiment, and the same elements are denoted by the same reference numerals.

The capsule-shaped casing 42 includes as its body the cylindrical casing 42a having the board-separation keeping function similar to that of the cylindrical casing 22a according to the second embodiment. The edges of the openings of the cylindrical casing 42a on both sides are closed with the dome-shaped casings 2b and 2c. The capsule-shaped casing 42 is similar to the capsule-shaped casing 22 of the capsule medical apparatus 21 according to the second embodiment except about the structure of the cylindrical casing 42a.

The cylindrical casing 42a has a battery supporting function of supporting the batteries 12a and 12b, which are incorporated, in addition to the board-separation keeping function. Specifically, as illustrated in FIG. 17, the cylindrical casing 42a includes a battery supporting portion 42b in a position opposed to the side portions of the batteries 12a and 12b. The battery supporting portion 42b is formed by forming the casing part thick, which is opposed to the side portions of the batteries 12a and 12b. In this case, the inner diameter of the battery supporting portion 42b is adjusted for the outer diameter of the batteries 12a and 12b. The battery supporting portion 42b sandwich the batteries 12a and 12b, which reduces instability of the batteries 12a and 12b. As a result, the relative movement of the batteries 12a and 12b and the contact springs 26a and 26b is reduced. This prevents the batteries 12a and 12b from being short-circuited or detached.

The cylindrical casing 42a is similar to the cylindrical casing 22a of the capsule medical apparatus 21 according to the second embodiment, except for the battery supporting function. In other words, the capsule medical apparatus 41 according to the fourth embodiment is similar to the capsule medical apparatus 21 according to the second embodiment, except for the battery supporting function. The method of manufacturing the capsule medical apparatus 41 is similar to the method of manufacturing the capsule medical apparatus 21 according to the second embodiment.

As explained above, in the fourth embodiment, the inner diameter of the casing part that is opposed to the side portions of the incorporated batteries of the cylindrical casing, which has the board-separation keeping function, is adjusted for the outer diameter of the incorporated batteries. The casing part sandwiches the incorporated batteries. Other aspects of the configuration are similar to those of the second embodiment. Accordingly, similar effects to those of the second embodiment are achieved and instability of the incorporated batteries in the casing can be reduced. This reduces relative movement of the incorporated batteries and the contacts in the casing. This prevents the incorporated batteries from being short-circuited and being detached.

Fifth Embodiment

A fifth embodiment of the present invention will be explained. In the first to fourth embodiments, the rigid boards are electrically connected through the flexible boards. In the fifth embodiment, interior wiring that extends to the fitting portions for the rigid boards are formed three-dimensionally on the inner wall of the cylindrical casing that sandwiches the rigid boards. The rigid boards are electrically connected through the three-dimensional interior wiring (hereinafter, three-dimensional wiring).

Figure 18:
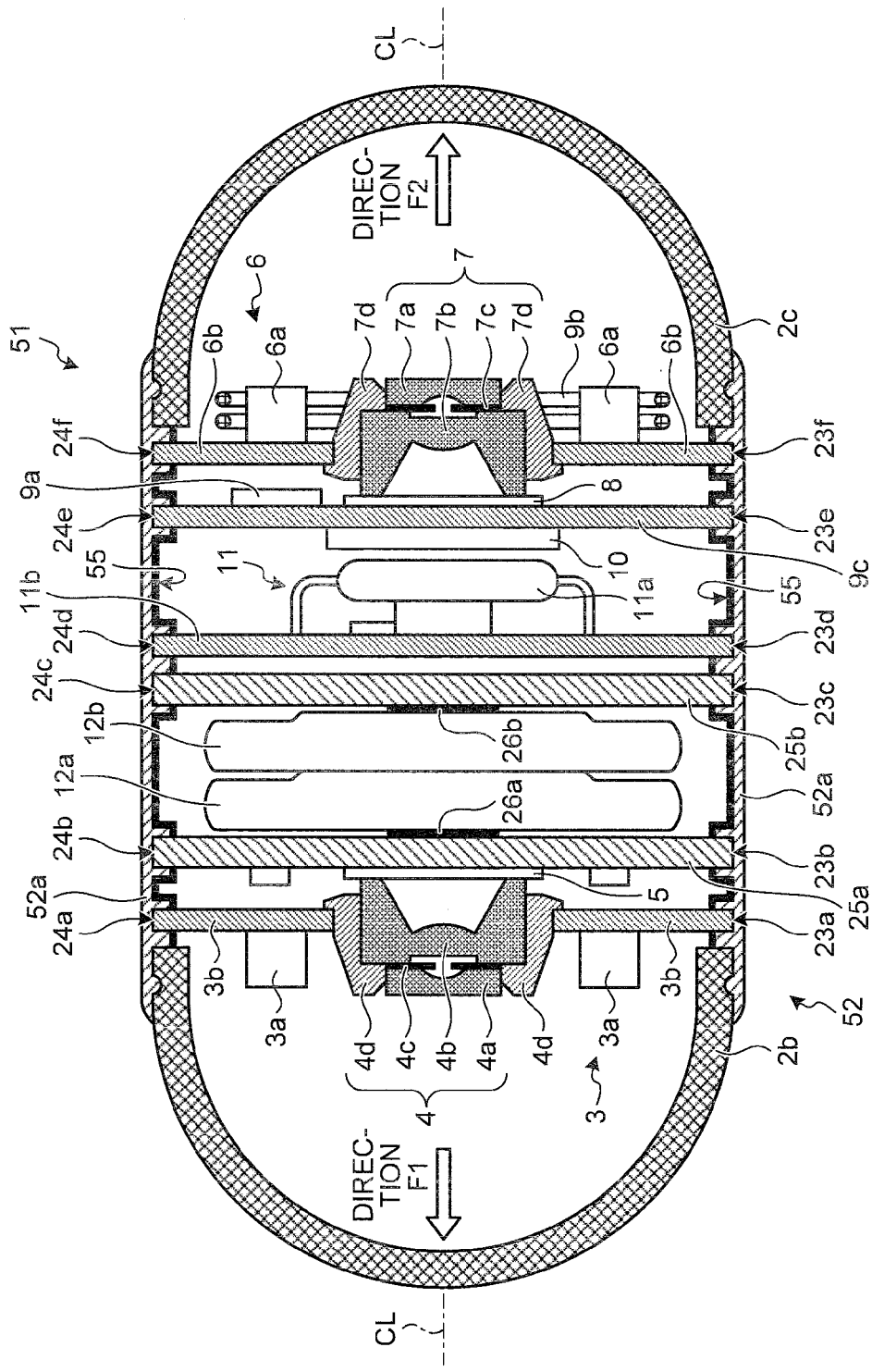
FIG. 18 is a schematic cross-sectional view that represents a configuration example of a capsule medical apparatus according to a fifth embodiment of the present invention.

FIG. 18 is a schematic cross-sectional view that represents a configuration example of a capsule medical apparatus according to the fifth embodiment of the present invention. As illustrated in FIG. 18, a capsule medical apparatus 51 according to the fifth embodiment includes a capsule-shaped casing 52 instead of the capsule-shaped casing 32 of the capsule medical apparatus 31 according to the third embodiment. The capsule-shaped casing 52 includes a cylindrical casing 52a having an inner wall on which three-dimensional wiring 55 are formed instead of the cylindrical casing 32a of the capsule medical apparatus 31 according to the third embodiment. In the capsule medical apparatus 51 according to the fifth embodiment, circuit wiring is formed on the surfaces of the rigid boards 3b, 6b, 9c, 11b, 25a, and 25b. The rigid boards 3b, 6b, 9c, 11b, 25a, and 25b are electrically connected through the three-dimensional wiring 55 of the cylindrical casing 52a instead of the flexible boards 13a to 13f. Other aspects of the configuration are the same as those of the third embodiment and the same elements are denoted by the same reference numerals.

The capsule-shaped casing 52 includes as its body the cylindrical casing 52a that has a similar structure to that of the cylindrical casing 32a according to the third embodiment. The edges of openings of the cylindrical casing 52a on both sides are closed with the dome-shaped casings 2b and 2c. The capsule-shaped casing 52 is similar to the capsule-shaped casing 32 of the capsule medical apparatus 31 according to the third embodiment, except for the structure of the cylindrical casing 52a.

The cylindrical casing 52a has the board-separation keeping function similar to that of the cylindrical casing 32a and a board connecting function of electrically connecting a plurality of rigid boards. Specifically, the cylindrical casing 52a has a board-separation keeping function similar to that of the cylindrical casing 32a, i.e., the fitting portions 23a to 23f and 24a to 24f on the inner wall of the cylindrical casing 52a. The cylindrical casing 52a further includes the three-dimensional wiring 55 for eclectically connecting the rigid boards. The three-dimensional wiring 55 are formed along the inner wall of the cylindrical casing 52a three-dimensionally and extend to the fitting portions 23a to 23f and 24a to 24f. The three-dimensional wiring 55 are electrically connected to the circuit wiring of the rigid boards 3b, 25a, 25b, 11b, 9c, and 6b, which are fitted to the fitting portions 23a to 23f and 24a to 24f, so that the rigid boards 3b, 25a, 25b, 11b, 9c, and 6b are electrically connected.

The cylindrical casing 52a is similar to the cylindrical casing 32a of the capsule medical apparatus 31 according to the third embodiment except that the cylindrical casing 52a includes the three-dimensional interconnects 55 on its inner wall. In other words, the capsule medical apparatus 51 according to the fifth embodiment is similar to the capsule medical apparatus 31 according to the third embodiment except that the rigid boards are electrically connected through the three-dimensional wiring 55 of the cylindrical casing 52a without the flexible boards 13a to 13f.

The method of manufacturing the capsule medical apparatus 51 is almost similar to the method of manufacturing the capsule medical apparatus 31 according to the third embodiment. In other words, in the fifth embodiment, the rigid boards 3b, 25a, 25b, 11b, 9c, and 6b, on which the circuit wiring is appropriately formed and necessary functional parts are mounted, and the batteries 12a and 12b are combined to assemble the internal parts of the capsule medical apparatus 51 as in the case of the third embodiment. Thereafter, the divided parts of the cylindrical casing 52a sandwich the internal parts and the rigid boards 3b, 25a, 25b, 11b, 9c, and 6b of the internal parts are fitted to the fitting portions 23a to 23f and 24a to 24f. This keeps the rigid boards 3b, 25a, 25b, 11b, 9c, and 6b separated, and electrically connects the rigid boards 3b, 25a, 25b, 11b, 9c, and 6b through the three-dimensional wiring 55. Other manufacturing steps are similar to those of the third embodiment.

Figure 19:
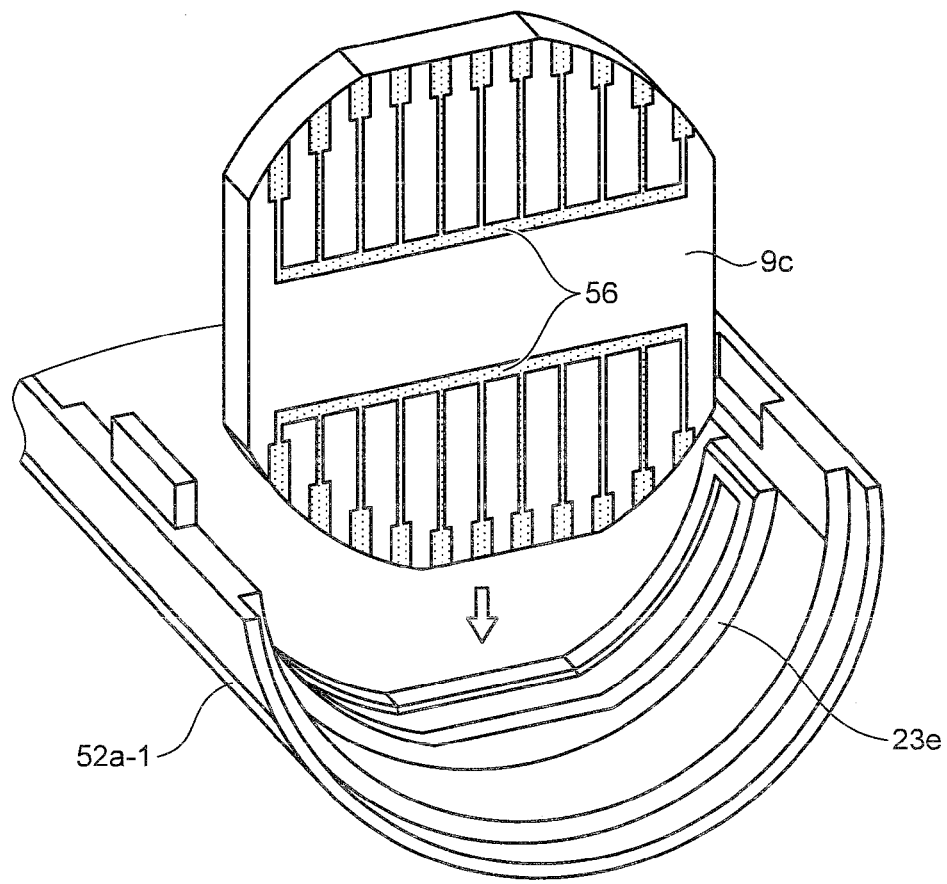
FIG. 19 is a schematic diagram exemplarily representing that a rigid boards is fitted to a fitting portion.
Figure 20:
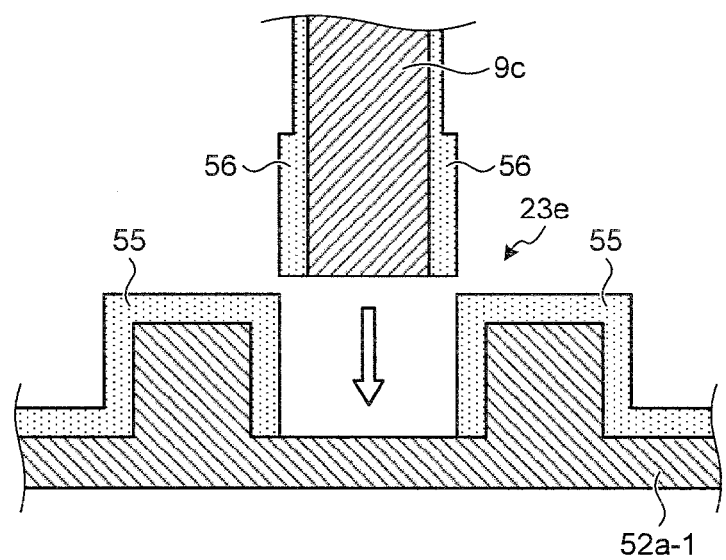
FIG. 20 is a schematic cross-sectional view exemplarily representing that the rigid board is fitted to the fitting portion, so that a three-dimensional wiring and a circuit wiring of the rigid board are electrically connected.

Electrical connection between the rigid boards through the three-dimensional wiring 55 is explained by exemplarily representing the case where the rigid board 9c is fitted to the fitting portion 23e of the cylindrical casing 52a. FIG. 19 is a schematic diagram exemplarily representing that the rigid board is fitted to the fitting portion of the cylindrical casing. FIG. 20 is a schematic cross-sectional view exemplarily representing that the rigid board is fitted to the fitting portion, so that the three-dimensional wiring and the circuit wiring of the rigid board are electrically connected. A divided part 52a-1 illustrated in FIG. 19 is one of a pair of separated members obtained by dividing the cylindrical casing 52a along the long axis CL of the capsule-shaped casing 52. Although it is not specifically illustrated in FIG. 19, the fitting portions 23a to 23f and the three-dimensional wiring 55 are formed on the inner wall of the divided part 52a-1.

The rigid board 9c includes a circuit wiring 56 on both front and back sides. The rigid board 9c is fitted to the fitting portion 23e of the divided part 52a-1 as illustrated in FIGS. 19 and 20. The three-dimensional wiring 55, which are formed on the inner wall of the divided part 52a-1, extend to the inner side of the fitting portion 23e. When the rigid board 9c is fitted to the fitting portion 23e, the rigid board 9c is electrically connected to the three-dimensional wiring 55 extending to the fitting portion 23e. In other words, the circuit wiring 56 on the rigid board 9c, which is fitted to the fitting portion 23e, is electrically connected to the three-dimensional wiring 55. As described above, the electrical contacts of the rigid board 9c are assured by fitting the rigid board 9c to the fitting portion 23e on which the three-dimensional wiring 55 are formed.

The three-dimensional wiring 55 extends to the fitting portions 23a to 23f and 24a to 24f on the inner wall of the cylindrical casing 52a, which is obtained by integrating the divided part 52a-1 and the remaining divided part (not shown). When the rigid boards 3b, 25a, 25b, 11b, 9c, and 6b are fitted to the fitting portions 23a to 23f and 24a to 24f, the circuit wiring of the respective rigid boards 3b, 25a, 25b, 11b, 9c, and 6b are electrically connected to the three-dimensional wiring 55 as in the case of the rigid board 9c. As a result, the rigid boards 3b, 25a, 25b, 11b, 9c, and 6b are electrically connected one another through the three-dimensional wiring 55 on the inner wall of the cylindrical casing 52a.

As explained above, in the fifth embodiment, the interior wiring extending to the fitting portions, to which the rigid boards are fitted, are formed three-dimensionally on the inner wall of the casing. When the rigid boards are fitted to the fitting portions, the rigid boards are electrically connected through the three-dimensional interior wiring (i.e., the three-dimensional wiring). Other aspects of the configuration are similar to those of the third embodiment. Thus, the similar effects to those of the third embodiment can be achieved, and the rigid boards can be made conductive easily by fitting the rigid boards to the fitting portions without connecting the rigid boards with the flexible boards. As a result, the number of steps of assembling the internal parts of the capsule medical apparatus can be reduced and the capsule medical apparatus can be manufactured more easily.

In the first to fifth embodiments, the batteries are arranged between the rigid boards. Alternatively, the part holders, which serve as the board-separation keeping units to keep the rigid boards separated, may hold the batteries in a space between the capsule-shaped casing and the internal parts (excluding the batteries), such as the rigid boards on which the functional parts are mounted.

Figure 21:
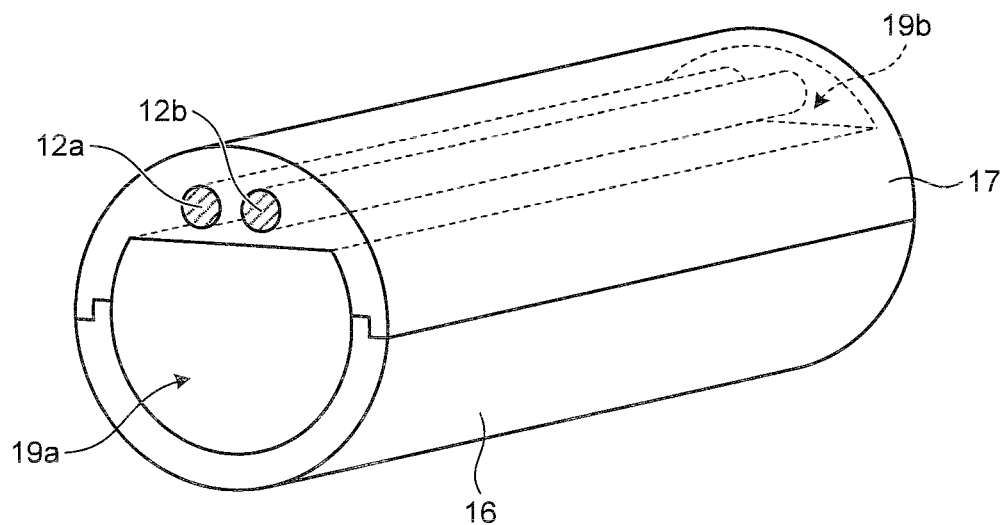
FIG. 21 is a schematic diagram that represents a first modification of the part holders, which serve as board-separation keeping units to keep the rigid boards separated.
Figure 22:
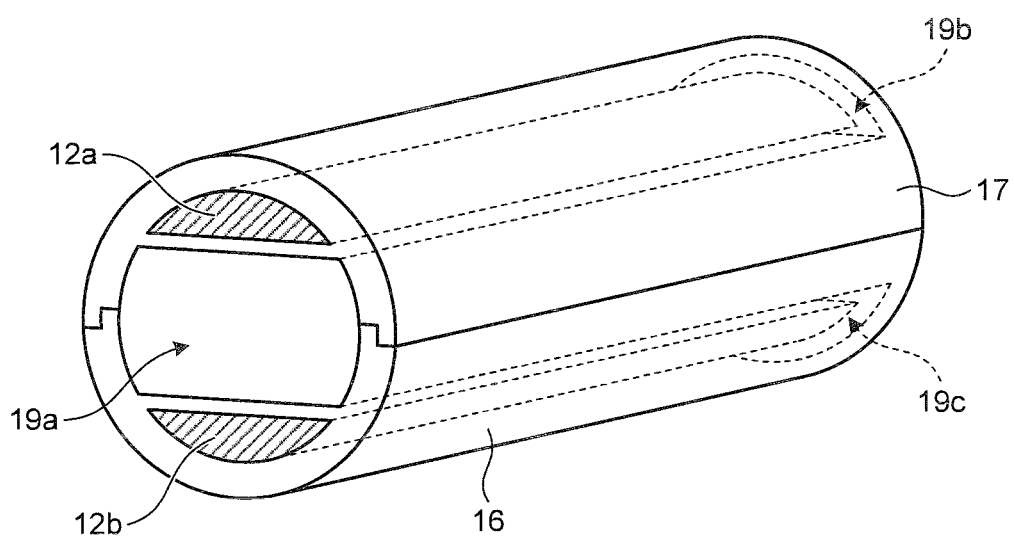
FIG. 22 is a schematic diagram representing a second modification of the part holders, which serve as the board-separation keeping units to keep the rigid boards separated.
Figure 23:
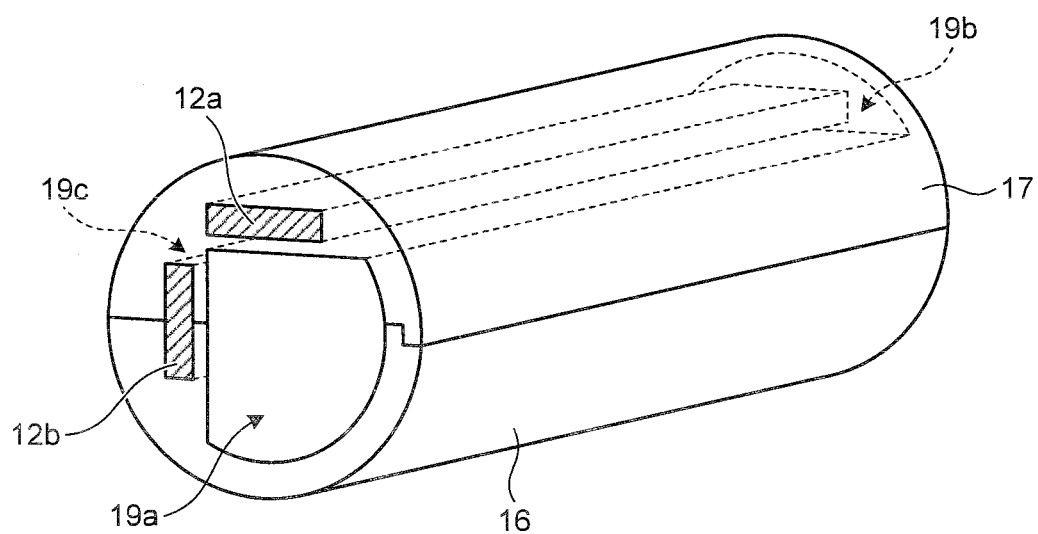
FIG. 23 is a schematic diagram representing a third modification of the part holders, which serve as the board-separation keeping units to keep the rigid boards separated.

FIG. 21 is a schematic diagram that represents a first modification of the part holders, which serve as the board-separation keeping units to keep the rigid boards separated. FIG. 22 is a schematic diagram that represents a second modification of the part holders, which serve as the board-separation keeping units to keep the rigid boards separated. FIG. 23 is a schematic diagram that represents a third modification of the part holders, which serve as the board-separation keeping units to keep the rigid boards separated. Although it is not specifically illustrated in FIGS. 21 to 23, the exterior wall surfaces of the part holders 16 and 17 in a pair are opposed (or contact) to the inner wall surface of the capsule-shaped casing.

As illustrated in FIG. 21, the part holders 16 and 17 in a pair may sandwich the rigid boards in a board holding space 19a and hold the batteries 12a and 12b in a battery holding space 19b, which is formed between the board holding space 19a and the inner wall surface of the capsule-shaped casing. In contrast, as illustrated in FIGS. 22 and 23, the part holders 16 and 17 in a pair may sandwich the rigid boards in the board holding space 19a and hold the batteries 12a and 12b respectively in the battery holding space 19b and a battery holding space 19c that are formed between the board holding space 19a and the inner wall surface of the capsule-shaped casing. The batteries 12a and 12b held by the part holders 16 and 17 are not limited to button batteries. Alternatively, cylindrical batteries as those illustrated in FIG. 21, convex batteries as those illustrated in FIG. 22, or cuboid batteries as those illustrated in FIG. 23 may be used.

In the first to fifth embodiments, the lens frame having a tapered outer shape is used as an optical frame of the optical system, and a plurality of lenses in different diameters are sequentially arranged in the lens frame from one with a small diameter. Alternatively, lenses in approximately same diameters may be arranged in a cylindrical lens frame.

Figure 24A:
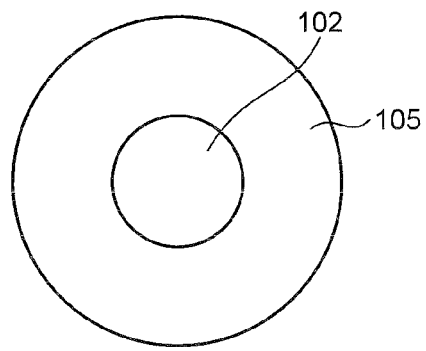
FIG. 24A is a top view that represents a modification of an optical system that is incorporated in the capsule medical apparatus according to the embodiments.
Figure 24B:
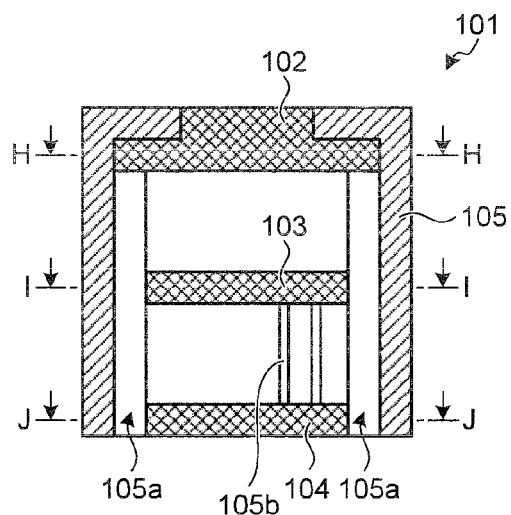
FIG. 24B is a side cross-sectional view of the optical system illustrated in FIG. 24A.
Figure 24C:
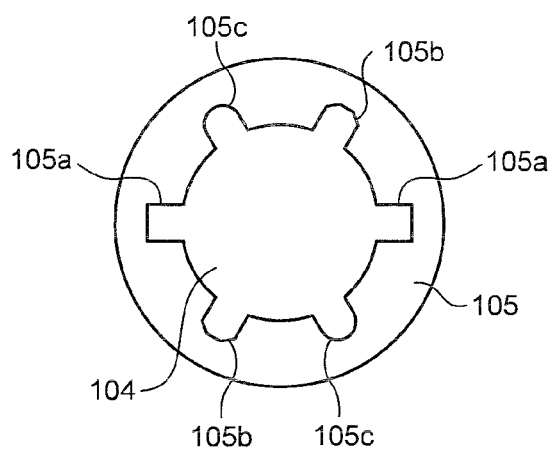
FIG. 24C is a bottom view of the optical system illustrated in FIG. 24A.
Figure 25:
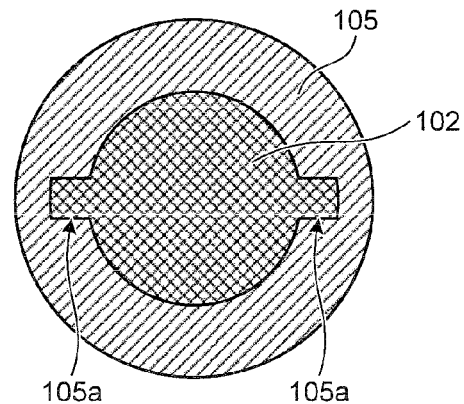
FIG. 25 is a schematic cross-sectional view, taken along H-H line, of the optical system illustrated in FIG. 24B.
Figure 26:
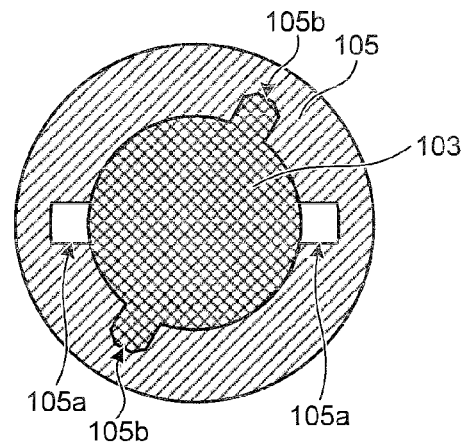
FIG. 26 is a schematic cross-sectional view, taken along I-I line, of the optical system illustrated in FIG. 24B.
Figure 27:
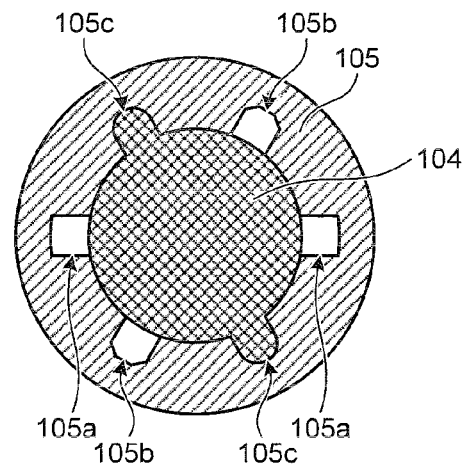
FIG. 27 is a schematic cross-sectional view, taken along J-J line, of the optical system illustrated in FIG. 24B.

FIG. 24A is a top view that represents a modification of the optical system that is incorporated in the capsule medical apparatus according to the embodiments. FIG. 24B is a side cross-sectional view of the optical system illustrated in FIG. 24A. FIG. 24C is a bottom view of the optical system illustrated in FIG. 24A. FIG. 25 is a schematic cross-sectional view, taken along H-H line, of the optical system illustrated in FIG. 24B. FIG. 26 is a schematic cross-sectional view, taken along I-I line, of the optical system illustrated in FIG. 24B. FIG. 27 is a schematic cross-sectional view, taken along J-J line, of the optical system illustrated in FIG. 24B.

As illustrated in FIGS. 24 to 27, an optical system 101, which is a modification, includes lenses 102, 103, and 104 in approximately the same diameter that focus light reflected from an object; and a cylindrical lens frame 105 that holds the lenses 102, 103, and 104 inside. The lens 102 is arranged on an upper end of the lens frame 105. The lens 102 is exposed from an opening on the upper end of the lens frame 105 and engaged with the inner wall of the upper end. The lens 102 includes protruding portions in the same shape as that of a groove 105a that is formed on the lens frame 105. The lens 102 is fitted to the upper end of the lens frame 105 with the protruding portions fitted to the grooves 105a. The lens 103 is a lens that is arranged below the lens 102, which is arranged in the lens frame 105. The lens 103 is configured to be engaged with the inner wall of the lens frame 105. The lens 103 includes protruding portions that are formed in the lens frame 105 and have the same shape as that of grooves 105b. The lens 103 is fitted to an inner portion (below the lens 102) of the lens frame 105 with the protruding portions fitted to the grooves 105b. The lens 104 is arranged in a lower end of the lens frame 105. The lens 104 is configured to be engaged with the inner wall of the lens frame 105. The lens 104 includes protruding portions in the same shape as that of grooves 105c, which are formed in the lens frame 105. The lens 104 is fitted to the lower end of the lens frame 105 with the protruding portions fitted to the grooves 105c.

The lens frame 105 is a cylindrical structure with open upper and lower ends. The lens frame 105 holds therein the lenses 102, 103, and 104. Specifically, the grooves 105a, 105b, and 105c in different shapes corresponding to different lenses are formed in the inner wall of the lens frame 105. The groove 105a is a groove in the same shape as that of the protruding portion of the lens 102 and extends from the lower end of the lens frame 105 to a portion near the upper end. The groove 105b is a groove in the same shape as that of the protruding portion of the lens 103 and extends from the lower end of the lens frame 105 to the position where the lens 103 is arranged. The groove 105c is a groove in the same shape as that of the protruding portion of the lens 104 and extends from the lower end of the lens frame 105 to the position where the lens 104 is arranged. The grooves 105a, 105b, and 105c are formed in different positions in the lens frame 105 as illustrated in FIGS. 25 to 27.

The lens 102 is fitted into the upper end of the groove 105a of the lens frame 105 having the above structure, the lens 103 is fitted into the upper end of the groove 105b, and then the lens 104 is fitted into the upper end of the groove 105c. Accordingly, the lenses 102, 103, and 104 are pressed against the lens frame 105 in their respective positions (upper end, middle, and lower wend) of the lens frame 105. Thus, the lenses 102, 103, and 104 are positioned in the lens frame 105.

In the optical system 101, which is a modification, the lenses 102, 103, and 104 can be positioned easily in the lens frame 105 by sequentially fitting the lenses 102, 103, and 104 to the lens frame 105 along the grooves 105a, 105b, and 105c without increasing the diameter of the lens frame from the top to the bottom. As a result, the optical system 101 can be assembled easily. The optical system 101 can be used instead of the optical systems 4 and 7.

In the first to fifth embodiments, heating the incorporated batteries is not considered. The incorporated batteries of the capsule medical apparatus may be heated to extend the time in which the incorporated batteries discharge. Specifically, a heat generator may be provided near the batteries 12a and 12b, which are incorporated in the capsule medical apparatus according to the embodiments, and the heat generator may heat the batteries 12a and 12b to extend the time in which the batteries 12a and 12b discharge. For example, a heating generating unit, such as a resistance wire, may be used as the heat generator. However, to achieve low power consumption, it is preferable that a part of the existing internal parts that generate a reactive power be used as a heat generator instead of providing a heat generator dedicated to heating the batteries 12a and 12b. In this case, a power supply controller, such as a regulator, an illuminating-unit drive circuit, a light emitter, a signal processing circuit, and a control circuit can be taken as examples of the heat generator.

Figure 28:
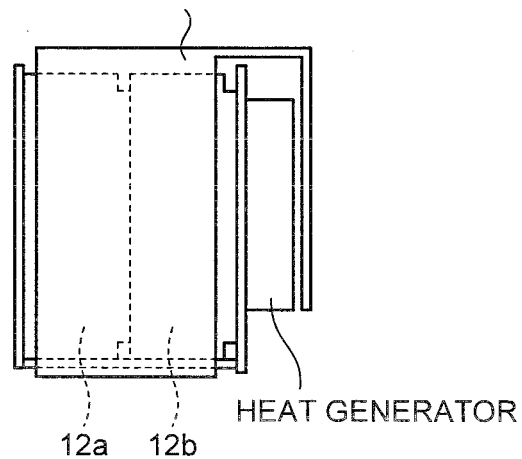
FIG. 28 is a schematic diagram that represents an example of a state where incorporated batteries and a heat generator are connected to each other through a heat conducting member.
Figure 29:
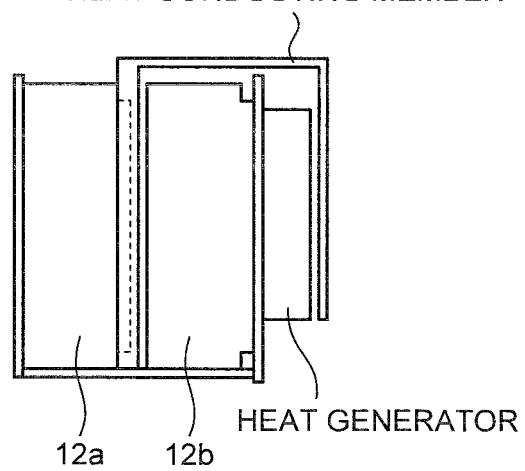
FIG. 29 is a schematic diagram that represents another example of the state where the incorporated batteries and the heat generator are connected to each other through the heat conducting member.

The heat generator may be thermally connected to the batteries 12a and 12b through a heat conducting member with high heat conductivity to transfer heat to the batteries 12a and 12b through the heat conducting member, so that the batteries 12a and 12b are efficiently heated. FIG. 28 is a schematic diagram that represents an example of a state where the incorporated batteries and the heat generator are connected to each other through the heat conducting member. FIG. 29 is a schematic diagram that represents another example of the state where the incorporated batteries and the heat generator are connected to each other through the heat conducting member. The heat conducting member may cover the batteries 12a and 12b as illustrated in FIG. 28 or may be sandwiched between the batteries 12a and 12b as illustrated in FIG. 29. In any of the cases, the heat generator can efficiently heat the batteries 12a and 12b through the heat conducting member. This extends the time in which the batteries 12a and 12b discharge. A member, such as metal or a graphite sheet, may be taken as the heat conducting member. However, because electric insulation between the batteries 12a and 12b and the heat generator needs to be ensured if a metallic member is used, it is preferable that a graphite sheet, which is an insulating member, be used.

In the first embodiment, the part holders in a pair, which have the board-separation keeping function, sandwich the rigid boards to keep the rigid boards separated. Alternatively, three or more part holders, which can be integrated into a board-separation keeping unit, may sandwich the rigid boards to keep the rigid boards separated.

In the second to fifth embodiments, the divided part in a pair, which are obtained by dividing the cylindrical casing having the board-separation keeping function into two parts along the long axis of the capsule medical apparatus, sandwich the rigid boards to keep the rigid boards separated. Alternatively, the rigid boards may be sandwiched by three or more divided parts, which can be integrated into a cylindrical member, to keep the rigid boards separated.

In the first to fifth embodiments, the rigid board is fitted to the concave fitting portions. Alternatively, concave portions may be formed on a side of the rigid board and the rigid board may be fitted to convex fitting portions that can be fitted to the concave portions.

In the first to fourth embodiments, the incorporated rigid boards are fitted to the fitting portions. Alternatively, the rigid boards incorporated in the capsule medical apparatus may be not fitted to the fitting portions by, for example, pressing the rigid boards but sandwiched by the part holders or the cylindrical casing to keep the rigid boards separated. In other words, the rigid boards sandwiched by the part holders or the cylindrical casing may have instability to some extent as long as the rigid boards are positioned in the capsule-shape casing.

In the first to fifth embodiments, a part of the circumference of the rigid board is sandwiched by the part holders or the cylindrical casing. Alternatively, the part holders or the cylindrical casing may sandwich the entire circumference of the rigid board.

In the first embodiment, the rigid boards are electrically connected through the flexible boards. Alternatively, three-dimensional wiring extending to each of the fitting portions may be formed on the inner walls of the part holders and the rigid boards that are fitted to the fitting portions may be electrically connected through the three-dimensional wiring. In other words, a capsule medical apparatus that is obtained by combining the first and fifth embodiments appropriately may be achieved.

In the first embodiment, the area of the part holder excluding the fitting portions has a thickness larger than that of the fitting portions. Alternatively, the area of the part holder excluding the fitting portions may have the minimum thickness. In other words, a capsule medical apparatus that is obtained by combining the first and third embodiments appropriately may be achieved.

In the first embodiment, the batteries are arranged between the positions where the part holders are engaged. Alternatively, the inner diameter of a portion of the part holder, the portion opposed to the side portions of the incorporated batteries, may be adjusted for the outer diameter of the incorporated batteries and the portion may sandwich the incorporated batteries. In other words, a capsule medical apparatus that is obtained by combining the first and fourth embodiments appropriately may be achieved.

In the first to fifth embodiments, the binocular capsule medical apparatuses that incorporate two solid-state imaging devices that can take image in different directions are exemplarily described. Alternatively, the capsule medical apparatuses according to the embodiments may be monocular capsule medical apparatuses that incorporate a single solid-state imaging device or a pantoscopic capsule medical apparatus that can take images in three or more different directions.

In the first to fifth embodiments, the capsule medical apparatuses that have the image-taking and wireless communication functions are exemplarily described. Alternatively, the capsule medical apparatuses according to the embodiments may be capsule pH measuring apparatuses that acquire pH information of living organisms, a capsule medication applying device having a function of supplying or injecting medicine into a living body, or a capsule sampling device that samples a substance of living body (body tissue).

In the second to fourth embodiments, the fitting portions to which the rigid boards of the internal parts of the capsule medical apparatus are respectively fitted sideways are provided to the inner wall of each of the divided parts in a pair constituting the cylindrical casing, which is a part of the capsule medical apparatus. Alternatively, fitting portions having sufficient fitting lengths for supporting the rigid boards may be provided on the inner wall of one of the divided parts in a pair of the cylindrical casing and the divided part without the fitting portions on the inner wall may be firmly fixed to the divided part with the fitting portions to which the rigid boards are respectively fitted sideways.

Figure 30:
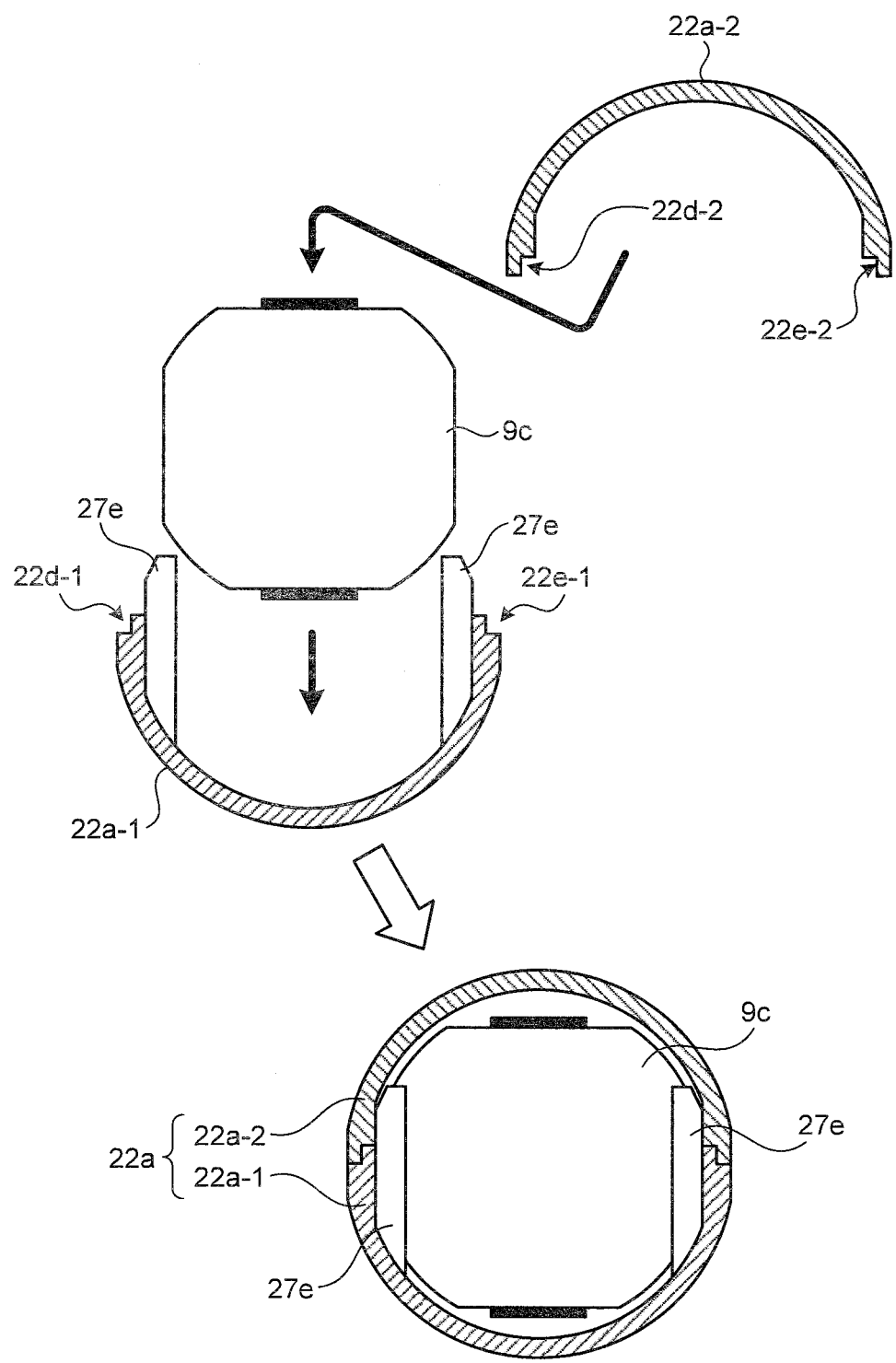
FIG. 30 is a schematic diagram exemplarily representing that the rigid boards is fitted to the fitting portion, which is provided to the inner wall of one of the divided parts in a pair, to sandwich the rigid board between the divided parts in a pair.

FIG. 30 is a schematic diagram exemplarily representing that the rigid board is fitted to the fitting portion, which is provided to the inner wall of one of the divided parts in a pair, to sandwich the rigid board between the divided parts in a pair. Specifically, in the capsule medical apparatus 21 according to the second embodiment, the cylindrical casing 22a, which is the body of the capsule-shaped casing 22, is made up of the divided parts 22a-1 and 22a-2. Fitting portions 27a to 27f, instead of the fitting portions 23a to 23f, to which the rigid boards 3b, 25a, 25b, 11b, 9c, and 6b are fitted respectively, are provided to the inner wall of the divided part 22a-1 out of the divided parts 22a-1 and 22a-2 in a pair. In this case, the fitting portions 24a to 24f are provided to the inner wall of the divided part 22a-2.

For example, the fitting portion 27e from the fitting portions 27a to 27f of the divided part 22a-1 has a fitting length sufficient to support the rigid board 9c as illustrated in FIG. 30. The rigid board 9c is fitted to the fitting portion 27e, so that the rigid board 9c is supported. Although it is not specifically illustrated, the fitting portions 27a, 27b, 27c, 27d, and 27f have structures similar to that of the fitting portion 27e. In other words, the fitting portion 27a has a fitting length sufficient to support the rigid board 3b and the rigid board 3b is fitted to the fitting portion 27a and supported, and the fitting portion 27b has a fitting length sufficient to support the rigid board 25a and the rigid board 25a is fitted to the fitting portion 27b and supported. The fitting portion 27c has a fitting length sufficient to support the rigid board 25b and the rigid board 25b is fitted to the fitting portion 27c and to supported, and the fitting portion 27d has a fitting length sufficient to support the rigid board 11b and the rigid board 11b is fitted to the fitting portion 27d and supported. Furthermore, the fitting portion 27f has a fitting length sufficient to support the rigid board 6b and the rigid board 6b is fitted to the fitting portion 27f and supported.

The divided part 22a-2 is fixed to the divided part 22a-1, which has the fitting portions 27a to 27f to which the rigid boards 3b, 25a, 25b, 11b, 9c, and 6b are fitted respectively, with the engaging portion 22d-1 and the engaging portion 22d-2 engaged with each other and the engaging portion 22e-1 and the engaging portion 22e-2 engaged with each other. As a result, the rigid boards 3b, 25a 25b, 11b, 9c, and 6b are sandwiched by the divided parts 22a-1 and 22a-2 in a pair.

For example, as illustrated in FIG. 30, the rigid board 9c being fitted sideways to the fitting portion 27e of the divided part 22a-1 is covered with the divided part 22a-2. The rigid board 9c may contact or not contact with the inner wall of the divided part 22a-2. In any of the cases, the rigid board 9c may be inhibited from being detached from the fitting portion 27e by the divided part 22a-2 that is firmly fixed to the divided part 22a-1. In other words, the rigid board 9c is sandwiched and held by the divided parts 22a-1 and 22a-2. Similarly, the divided parts 22a-1 and 22a-2 in a pair sandwich the rigid boards 3b, 25a, 25b, 11b, and 6b as they sandwich the rigid board 9c.

If the divided parts 22a-1 and 22a-2 in a pair configured as described above are used and the divided part 22a-2 is fixed to the divided part 22a-1 after the internal parts 28 are fixed to the divided part 22a-1, it is unnecessary to visually confirm how the rigid boards 3b, 25a, 25b, 11b, and 6b of the internal parts 28 are fitted. Accordingly, the divided parts 22a-1 and 22a-2 can be fixed easily. As a result, the capsule medical apparatus 21 can be assembled more easily. This effect can be achieved in the third and fourth embodiments using a similar configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus comprising:
   a capsule-shaped casing;
   a plurality of rigid boards on which functional parts are mounted; and
   a plurality of board-separation keeping units that sandwich the rigid boards to keep the rigid boards separated, wherein
   the board-separation keeping units include a plurality of fitting portions that are fitted respectively to the rigid boards, and include engaging portions that protrude across the inside of the capsule-shaped casing and are engaged with each other, and
   the fitting portions are fitted respectively to the rigid boards with the board-separation keeping units being engaged with each other by the engaging portions.

2. The capsule medical apparatus according to claim 1, wherein the fitting portions are fitted to at least a part of circumferences of the rigid boards.

3. The capsule medical apparatus according to claim 1, wherein the board-separation keeping units contain a minimum-thickness area in at least a part of an area excluding the fitting portions.

4. The capsule medical apparatus according to claim 1, wherein
   the board-separation keeping units include interior wiring that extends to at least the fitting portions, and
   the rigid boards are fitted respectively to the fitting portions and are electrically connected to the interior wiring.

5. The capsule medical apparatus according to claim 1, further comprising a battery that supplies electric power to the functional parts, wherein the board-separation keeping units sandwich the rigid boards and support the battery.

6. The capsule medical apparatus according to claim 1, wherein the board-separation keeping units are a plurality of divided parts obtained by dividing an integrated board separation keeping unit that sandwiches the rigid boards to keep the rigid boards separated, along a long axis of the capsule medical apparatus.

7. The capsule medical apparatus according to claim 1, wherein the board-separation keeping units serve as the capsule-shaped casing that houses therein at least the rigid boards.

8. The capsule medical apparatus according to claim 7, wherein the board-separation keeping units are integrated by laser welding.

* * * * *